(12) United States Patent
Alipour et al.

(10) Patent No.: US 10,513,696 B2
(45) Date of Patent: Dec. 24, 2019

(54) *LUCILIA SERICATA* COLLAGENASE

(71) Applicants: Hamzeh Alipour, Bushehr (IR); Abbasali Raz, Tehran (IR); Navid Dinparast Djadid, Tehran (IR); Sedigheh Zakeri, Tehran (IR)

(72) Inventors: Hamzeh Alipour, Bushehr (IR); Abbasali Raz, Tehran (IR); Navid Dinparast Djadid, Tehran (IR); Sedigheh Zakeri, Tehran (IR)

( * ) Notice: Subject to any disclaimer, the term of this patent is extended or adjusted under 35 U.S.C. 154(b) by 5 days.

(21) Appl. No.: 15/410,697

(22) Filed: Jan. 19, 2017

(65) Prior Publication Data

US 2017/0267988 A1   Sep. 21, 2017

Related U.S. Application Data

(60) Provisional application No. 62/340,536, filed on May 24, 2016.

(51) Int. Cl.
*C12N 9/64* (2006.01)
*A61K 38/00* (2006.01)

(52) U.S. Cl.
CPC .... *C12N 9/6416* (2013.01); *C12Y 304/24007* (2013.01); *A61K 38/00* (2013.01)

(58) Field of Classification Search
None
See application file for complete search history.

(56) References Cited

U.S. PATENT DOCUMENTS 5,453,371 A   9/1995   Shibano et al.
7,144,721 B1   12/2006   Pritchard

OTHER PUBLICATIONS

GenBank Accession No. KA649448 for *Musca domestica* ALHF_11207.g6231 mRNA, Aug. 22, 2013 [online], [retrieved on Jun. 5, 2018], retrieved from the Internet: <URL: //www.ncbi.nlm.nih.gov/nuccore/Ka649448>. (Year: 2013).*
GenBank Accession No. KA646105 for *Musca domestica* ALHF_03312.g2041 mRNA, Aug. 22, 2013 [online], [retrieved on Jun. 5, 2018], retrieved from the Internet: <URL: //www.ncbi.nlm.nih.gov/nuccore/Ka646105>. (Year: 2013).*
Stephen Britland, RecombinantLucilia SericataChymotrypsin in a Topical Hydrogel Formulation Degrades Human Wound Eschar Ex Vivo, Biotechnology Progress, Apr. 2001, vol. 27, No. 3, pp. 870-874.
Kuniko Yoshihara, Cloning and nucleotide sequence analysis of the colH gene from Clostridium histolyticum encoding a collagenase and a gelatinase, Journal of bacteriology, 1994, vol. 176, No. 21, pp. 6489-6496.
G. Telford, Degradation of eschar from venous leg ulcers using a recombinant chymotrypsin from Lucilia sericata, British Journal of Dermatology, 2010, vol. 163, Issue 3, pp. 523-531.

* cited by examiner

*Primary Examiner* — Angela M. Bertagna
(74) *Attorney, Agent, or Firm* — Bajwa IP Law Firm; Haris Zaheer Bajwa

(57) ABSTRACT

One complementary DNA (cDNA) encodes a collagenase enzyme of *Lucilia sericata* that includes an identified sequence. Optionally, the cDNA is applied to wound healing.

3 Claims, 6 Drawing Sheets

Specification includes a Sequence Listing.

FIG. 3

LUCILIA SERICATA COLLAGENASE

CROSS REFERENCE TO RELATED APPLICATION

This application claims the benefit of priority from U.S. Provisional Patent Application No. 62/340,536, filed on May 24, 2016, and entitled "*LUCILIA SERICATA* COLLAGENASE FOR THERAPEUTICALLY APPLICATION," which is incorporated herein by reference in its entirety.

TECHNICAL FIELD

The present disclosure generally relates to the field of cDNA sequencing and particularly to a cDNA derived from an insect of the species *Lucilia sericata* which encodes a collagenase enzyme, and a method for identifying cDNA sequence of *Lucilia sericata* collagenase.

BACKGROUND

Larval therapy also known as maggot therapy is a type of biotherapy involving the introduction of live, disinfected fly larvae into non-healing skin and soft tissue wounds of a human or animal for the purpose of disinfection and debridement or cleaning out the necrotic (dead) tissue within a wound. From a clinical point of view, major effects of larval therapy have been ascribed to their antibacterial and debriding mechanisms. In regard to the latter function, it has been speculated that once larvae are introduced into the wound, they secrete proteolytic enzymes that enable them to degrade and ingest necrotic tissues.

Collagenase (MMP1) is a member of matrix metalloproteinase (MMP) and is highly expressed in the salivary glands of *Lucilia sericata* once the larva gets in contact with wounds. Its expression is associated with contact to injuries. A unique characteristic of collagenase is its ability to degrade type I, II, III and IV collagens. Therefore, in the cases where collagen may be generated in more than the required amount or produced in unsuitable sites, utilizing an injectable collagenase or its ointment may be helpful in degradation of collagen. Also, collagenase, both in vitro and vivo, demonstrates certain therapeutic properties in wound healing and some diseases, for example, Peyronie's Disease, glaucoma, intervertebral disc herniation, burns, keloid, Dupuytren's disease, nipple pain, cellulite, lipoma, etc.

Although debridement treatment using the larvae of *Lucilia sericata* has become a widely accepted clinical practice, live larvae are unpleasant to many patients. Also, use of live larvae on wounds and the introduction of their crude secretions into wounds, which inevitably occurs when the larvae are used, are unacceptable to many patients and many medical practitioners. The use of live organisms also increases risk of infection or allergic reactions in the patient. In addition, the *Lucilia sericata* species of flies plays can be agent of facultative myiasis in humans and animals. There is, therefore, a need in the art for identification of collagenase gene sequences from *Lucilia sericata* larvae.

SUMMARY

The following brief summary is not intended to include all features and aspects of the present application, nor does it imply that the application must include all features and aspects discussed in this summary.

The present disclosure describes, according to a general aspect, a complementary DNA (cDNA) that can encode a collagenase enzyme of *Lucilia sericata*. In an implementation, the cDNA may include the nucleotide sequence set forth in SEQ ID No.1.

The above general aspect may include one or more of the following features. The cDNA may have, for example, 1932 nucleotides and the collagenase of *Lucilia sericata* encoded by described cDNA may include an amino acid sequence as set forth in SEQ ID No.2 which has 404 amino acid residues.

The present disclosure describes, in another aspect, a method for identifying the cDNA that can encode the collagenase enzyme of *Lucilia sericata*. In an implementation, the method can include extracting RNA from salivary glands of *Lucilia sericata*; synthesizing cDNA from extracted RNA; identifying middle part of the cDNA sequence of *Lucilia sericata* collagenase; identifying 3' end of cDNA sequence of *Lucilia sericata* collagenase through rapid amplification of cDNA ends technique (RACE); identifying 5' end of *Lucilia sericata* collagenase gene through rapid amplification of genomic ends technique (RAGE); and identifying full length cDNA sequence of *Lucilia sericata* collagenase as shown in SEQ ID No.1.

According to other implementations, identification of 5' end of *Lucilia sericata* collagenase gene may be carried out by using a plurality of genome walking primers which may be selected from the group consisting of GWA (SEQ ID No.14), GWB (SEQ ID No.15), GWC (SEQ ID No.16), GWD (SEQ ID No.17), GWE (SEQ ID No.18), GWF (SEQ ID No.19) and GWG (SEQ ID No.20).

BRIEF DESCRIPTION OF DRAWINGS

While the specification concludes with claims particularly pointing out and distinctly claiming the subject matter that is regarded as forming the present application, it is believed that the application will be better understood from the following description taken in conjunction with the accompanying DRAWINGS, where like reference numerals designate like structural and other elements, in which:

FIG. 3 shows the alignment of amino acid sequences of *Lucilia sericata* collagenase (MMP1) against MMPs sequences from different organisms like insects, mammalian and bacteria with and amino acid sequence as set forth in SEQ ID NO. 34 for *L. sericata* MMP1, SEQ ID NO. 35 for *M. domestica* MMP14, SEQ ID NO. 36 for *T. castaneum* MMP1, SEQ ID NO. 37 for *C. quinquefasciatus* MMP1, SEQ ID NO. 38 for *B. mori* MMP 1, SEQ ID NO. 39 for *D. melanogaster* MMP1, SEQ ID NO. 40 for *Homo sapiens* MMP1, SEQ ID NO. 41 for *Homo sapiens* MMP8, SEQ ID NO. 42 for *Homo sapiens* MMP13, SEQ ID NO. 43 for *Homo sapiens* MMP2, SEQ ID NO. 44 for *Homo sapiens* MMP9, SEQ ID NO. 45 for *Homo sapiens* MMP19, SEQ ID NO. 46 for *C. histolyticum* colH, and SEQ ID NO. 47 for *C. histolyticum* colG.

DETAILED DESCRIPTION

The basic mechanism of larval debridement may be described, without subscribing to any particular scientific theory, as follows. Digestive juices secreted by larvae during the feeding process contain a variety of proteolytic enzymes that selectively debride necrotic tissue and leave viable tissue unharmed. This mechanism suggests that proteases may play a significant role in wound healing process that is induced by larval secretion. One of the proteolytic enzymes identified in the larval secretion belongs to metalloproteinase family. Collagenase (MMP1), as a member of matrix metalloproteinase family, is highly expressed in the salivary glands of *Lucilia sericata* once larva is introduced into a wound, and its expression is associated with their introduction into injuries.

Directed to obviating some limitations of larval therapy, such as cost, complexity of use, and patient reticence, disclosed herein is a complementary DNA (cDNA) which may encode a collagenase enzyme of *Lucilia sericata*, and a method to identify the cDNA sequence of *Lucilia sericata* collagenase (MMP1) for producing recombinant *Lucilia Sericata* collagenase.

Figure 1:
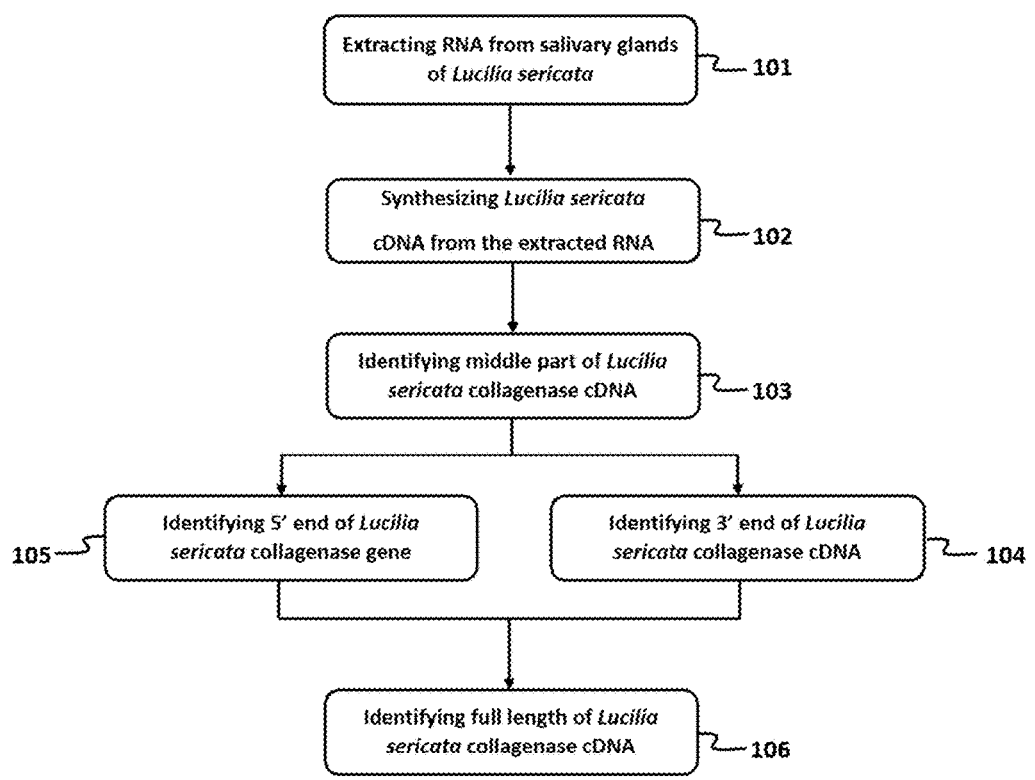
FIG. 1 is a flowchart of an example of a method for identifying sequence of *Lucilia sericata* collagenase cDNA, according to one or more aspects of the present disclosure.

FIG. 1 is a flowchart of an example of a method for identifying cDNA sequence of *Lucilia sericata* collagenase, consistent with exemplary implementations of the present disclosure.

Referring to FIG. 1, identifying cDNA sequence of *Lucilia sericata* collagenase may include extracting RNA from salivary glands of *Lucilia sericata* (step 101); synthesizing *Lucilia sericata* collagenase cDNA from the extracted RNA (step 102); identifying middle part of the *Lucilia sericata* collagenase cDNA (step 103); identifying 3' end of the *Lucilia sericata* collagenase cDNA (step 104); identifying 5' end of *Lucilia sericata* collagenase gene (step 105); and identifying full length of *Lucilia sericata* collagenase cDNA (step 106).

Referring to step 101, in an exemplary implementation, for extracting RNA from salivary glands of *Lucilia sericata*, *Lucilia sericata* larvae may be reared, whereupon their salivary glands may be dissected for extracting RNA from them. In an aspect, instar *Lucilia sericata* larvae can be reared under constant temperature and humidity. In one implementation, *Lucilia sericata* larvae may be exposed, for example, to 12 hours light/dark photo cycles at a temperature between, for example, 18° C. and 25° C. and a relative humidity between, for example 40% and 50%. The larvae may be fed, for example, chicken liver.

In one implementation, in order to dissect salivary glands, the instar larvae may first be anesthetized on ice and then decapitated. Dissection may be performed in, for example, a cold phosphate buffer saline (PBS) with a pH of 7-7.8. Salivary glands may be dissected, for example, 48 hours after feeding, e.g., on a body of a dead mouse. Thereafter, different biological replicates, each consisting of salivary glands from larvae, may be collected and frozen at, for example, −70° C. Then, in order to extract RNA for performing standard reverse transcription PCR (RT-PCR), total RNA may be extracted from salivary glands of first instar of larvae with an RNA purification kit, for example, according to the manufacturer's protocol.

In addition, genomic DNA contamination may be checked by exon-exon junction primers after each RNA extraction. To this end, in an example implementation, a volume of 2 μL of total RNA may be adjusted, for example, to 20 μL by adding (assuming the 20 μL example) 18 μL of RNase-free double distilled water (DDW). In an implementation, RNA may then be incubated, for example, at 75° C. for 5 minutes to remove secondary structures, and may then be immediately placed on ice.

Referring to step 102, for synthesizing cDNA from extracted RNA, reverse transcription (RT) may be done by applying the oligo dT (a short sequence of deoxy-thymidine nucleotides), random hexamer, or gene-specific primer (GSP) as primers. In an aspect, RT mix (reverse transcriptase enzyme, ribonuclease inhibitor, deoxy-nucleoside triphosphate (dNTP) solution, reverse transcription buffer, and primer) may be added to the cooled RNA, and reverse transcription may be started in a thermal cycler with the following exemplary program: 25° C. for 10 minutes, 42° C. for 60 minutes, and 70° C. for 10 minutes. Consequently, cDNA may be produced from the extracted RNA.

According to step 103, middle part of the synthesized cDNA of *Lucilia sericata* collagenase may be identified as follows. Because the *Lucilia sericata* genome has not yet been sequenced, primers must be designed for identifying the synthesized cDNA of *Lucilia sericata* collagenase. In an exemplary implementation, for designing primers, the RNA sequence of collagenase of different insects may be aligned by a bioinformatics software. After analysis, different regions may be chosen as highly conserved regions for designing the gene-specific primers. Then different forward and reverse primers may be designed for identification of middle part of cDNA by using different programs.

After different forward and reverse primers have been designed, by applying gene-specific primers to the synthesized cDNA, the middle part of the collagenase cDNA may be amplified by polymerase chain reaction (PCR). In an implementation, the PCR mixture can include PCR buffer, a forward primer, a reverse primer, $MgCl_2$, DNA polymerase, dNTPs (deoxy-nucleoside triphosphate), a cDNA template and double distilled water (DDW) for adjusting volume.

A PCR program for amplifying middle part of the collagenase cDNA may be described as follows. First, the PCR mixture may be placed in a thermal cycler at, for example, 94° C. for a duration as an initialization step, followed by a number of cycles of denaturation DNA templates, then annealing the primers to DNA templates, and then applying an extension step for synthesizing new DNA strand. The duration in the initialization step can be, for example, 5 minutes. An example number of cycles of denaturation DNA templates is 35. The denaturation step may be performed, for example, by placing PCR mixture at 94° C. for 30 seconds. Annealing the primers to DNA templates may be performed at, for example, 55-65° C., and may be maintained, for example, for 40 seconds. Extension of middle part of collagenase cDNA can be performed for example, at 72° C. for 80 seconds. Assuming the example 35 cycles for the PCR program, after finishing 35 cycles of the PCR program, in the last cycle, the PCR products, which are the middle part of *Lucilia sericata* collagenase cDNA, can be further incubated to allow the completion of DNA synthesis. The incubation can be at, for example, 72° C. for 10 minutes. After the PCR products are further incubated, the amplified products may further be purified using a DNA gel purification kit.

In an another implementation, the purified PCR products may be cloned into a plasmid vector by applying purified PCR products to the plasmid vector at a molar ratio of, for example, 3:1 at 22° C. for 40 minutes and then the recombinant plasmid may be transformed into freshly prepared *Escherichia coli* (*E. coli*) host cells. Recombinant clones may then be selected by using a screening method. In an implementation, the clones may be confirmed by universal and GSP primers and the recombinant clones that have the PCR products may be picked up and their plasmids may be extracted and purified; after that, the insertion of the appropriate DNA into plasmids may be identified through sequencing.

Figure 2:
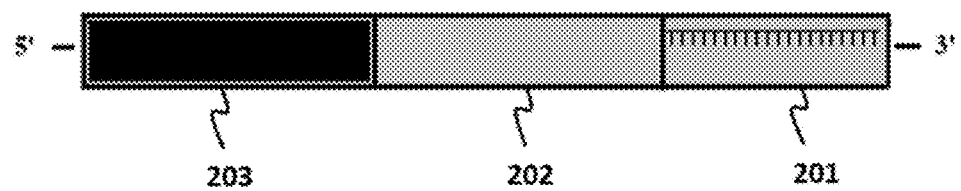
FIG. 2 shows the structure of linker primer as set forth in SEQ ID NO. 27 used in rapid amplification of cDNA ends (RACE) method for identifying 3' end of the *Lucilia sericata* collagenase cDNA.

In step 104, identifying 3' end of cDNA of *Lucilia sericata* collagenase may be performed by a rapid amplification of cDNA ends (RACE) method. For determining directionality of cDNA strand, the 3' end designated the end of a cDNA strand that is terminated at the hydroxyl group of the third carbon in the sugar-ring. In this step, the total RNA from *Lucilia sericata* salivary glands may be extracted as explained in step 101. In an implementation, synthesizing cDNA from extracted RNA can be done by using a Linker primer through a procedure which was explained according to step 102. FIG. 2 shows the structure of a Linker primer with different parts, such as an oligo thymidine sequence According to step 105, identifying 5' end of *Lucilia sericata* collagenase gene may be carried out by a rapid amplification of genomic ends (RAGE) method. For determining the directionality of cDNA strand, the 5' end designated the end of the cDNA strand that has the fifth carbon in the sugar-ring of deoxyribose at its terminus. At first, after DNA extraction from *Lucilia sericata*, one gene-specific primer may be used as a primer for making a specific single strand of DNA template. In order to amplify 5' end of *Lucilia sericata* collagenase gene and based on the repeated sequences in promoter region of different organisms, several genome walking primers (GWP) can be designed for performing the PCR. Then, an amount, for example 1 µL, of the DNA template may be added to several micro tubes. Subsequently, an amount, for example 1.6 µl, of each genome walking primers and 3.2 µl of mixed solution (dNTP, MgCl$_2$, DNA polymerase, dNTPs, and PCR buffer) may be added to reactions for performing PCR. TABLE 1 shows the first PCR program for identifying 5' end of *Lucilia sericata* collagenase gene by using genome walking primers in RAGE method. In the last cycle, the PCR products may be further incubated, for example, at 72° C. for 10 minutes.

TABLE 1

The program of PCR for identifying 5' end of *Lucilia sericata* collagenase gene by using genome walking primers

| | Cycles | | | | | | | | | | | | |
|---|---|---|---|---|---|---|---|---|---|---|---|---|---|
| | 10 cycles from step2 to 3 | | | | | | | 7 cycles from step 5 to 13 | | | | | |
| Step | 1 | 2 | 3 | 4 | 5 | 6 | 7 | 8 | 9 | 10 | 11 | 12 | 13 |
| Temperature (° C.) | 94 | 34 | 72 | 72 | 94 | 15 | 72 | 94 | 65 | 72 | 94 | 36 | 72 |
| Time | 4 min | 1 min | 1 min | 5 min | 30 sec | 30 sec | 3 min | 30 sec | 30 sec | 30 sec | 30 sec | 60 sec | 3 min |

201, an Inner primer attachment site 202 and an Outer primer attachment site 203. Referring to FIG. 2, oligo thymidine sequence 201 may be used as a primer for attaching to the poly adenine tail of RNA for synthesizing cDNA. Inner primer attachment site 202 and Outer primer attachment site 203 may be used as sites for attaching Inner and Outer primers for amplifying 3' end of cDNA of *Lucilia sericata* collagenase.

In order to identify 3' end of cDNA of *Lucilia sericata* collagenase, based on the middle part of the cDNA that was sequenced in the step 103, forward and reverse primers may be designed. Outer primer as reverse primer and the outermost primer of gene-specific primers (designed based on middle part sequence) as forward primer may be applied for first round of PCR for the amplification of 3' end of the cDNA of *Lucilia sericata* collagenase.

Afterwards, PCR products of the first round of PCR for the amplification of 3' end of the cDNA can be used for the second round of PCR as a nested PCR for validating the first round of PCR. Therefore, for the second round of PCR, the combination of inner primer as reverse primer and other gene-specific primers (designed based on middle part sequence) as forward primers confirms the first round of PCR in several separate reactions through the size of PCR products according to their band in electrophoresis gel.

After confirmation, according to step 103 as described, the products of the first round of PCR may be cloned to a vector, and then host cells may be transformed by the recombinant vectors. After screening the transformed host cells and extracting recombinant vectors which have the appropriate insertion, they may be sequenced for identifying 3' end of cDNA of *Lucilia sericata* collagenase.

Next, a nested PCR may be performed, for example, with two serial PCR reactions. Assuming two serial PCR reactions, for the first reaction of nested PCR, the PCR products of the reactions with genome walking primers from each micro tube may be diluted, for example, by ¹⁄₂₅ (volume/volume) with double distilled water. Then, 1 µL of the diluted product may be used as a template for performing PCR with the first nested PCR primer as a forward primer and one of the gene-specific primers as reverse primers according to the following PCR program. First, the PCR mixture (DNA template, forward primer, reverse primer, dNTP, MgCl$_2$, dNTPs, and PCR buffer, DNA polymerase) may be placed in a thermal cycler, for example, at 94° C. for 5 minutes as an initialization step followed by a plurality of cycles, for example 35 cycles, of denaturation DNA templates, followed by annealing the primers to DNA templates, and then an extension step for synthesizing new DNA strand. The denaturation step may be performed by placing PCR mixture at, for example, 94° C. for 30 seconds; annealing the primers to DNA templates may be done at, for example, 58° C. for 30 seconds; and extension of new strands as 5' end of collagenase cDNA may be done at, for example, 72° C. for 80 seconds. After finishing 35 cycles of the PCR program, in the last cycle, the PCR products, which are the middle part of *Lucilia sericata* collagenase cDNA, can be further incubated, for example, at 72° C. for 10 minutes to allow the completion of DNA synthesis.

Regarding the second reaction of the nested PCR, in an implementation, the PCR products of the first nested PCR may be diluted to, for example ¹⁄₂₅ for each micro tube. The diluted products may then be used as a template for second nested PCR reaction with second nested primer as forward primer and another gene-specific primer as reverse primer with the same PCR program as first reaction of nested PCR.

Next, the PCR products of different genome walking primers (GW) may be analyzed on agarose gel and the PCR products that have sharp bands may be cloned into a vector and then host cells may be transformed by the recombinant vectors according to the method described in connection with step 103. After screening the transformed host cells and extracting recombinant vectors that have the appropriate insertion, they may be sequenced for identifying 5' end of *Lucilia sericata* collagenase gene.

In step 106, full length sequence of cDNA and gene of *Lucilia sericata* collagenase may be identified based on the identification of the middle part and 3' end of *Lucilia sericata* collagenase cDNA and 5' end of *Lucilia sericata* collagenase gene and assembling them by a software. Therefore, the assembled sequence may be considered as full length cDNA sequence of collagenase (MMP1) of *Lucilia sericata* and it may be analyzed and its coding sequence (CDS) may be determined. Accordingly, specific primers may be designed to amplify the CDS and open reading frame (ORF) of *Lucilia sericata* collagenase gene for identifying full length sequence of collagenase cDNA and gene.

Next, for amplifying full length sequence of cDNA and gene of *Lucilia sericata* collagenase, the RNA extraction and cDNA synthesis may be performed as explained according to step 101. In addition, DNA extraction from salivary glands of *Lucilia sericata* may be done by using, for example, a DNA extraction kit. Therefore by using the synthesized cDNA and the extracted DNA, the PCR may be done by using specific primers. Sequencing of PCR products may be done as explained in step 102. Accordingly, full length of cDNA and gene may be determined.

EXAMPLES

Example 1: Identifying cDNA Sequence of *Lucilia sericata* Collagenase

In this example, cDNA sequence of *Lucilia sericata* collagenase was identified with following steps: extracting RNA from salivary glands of *Lucilia sericata*; synthesizing *Lucilia sericata* cDNA from the extracted RNA; identifying middle part of *Lucilia sericata* collagenase cDNA, identifying 3' end of the *Lucilia sericata* collagenase cDNA; identifying 5' end of the *Lucilia sericata* collagenase gene; and identifying full length of *Lucilia sericata* collagenase cDNA.

In the first step, for extracting RNA from salivary glands of *Lucilia sericata*, first instar *Lucilia sericata* larvae were used from a colony reared in the National Insectariums of Iran (NII) under constant temperature and humidity. Regarding temperature and humidity, *Lucilia sericata* flies were exposed to 12-hour light/dark photo cycles at 22.5° C. and a relative humidity of 45%. The larvae were fed with chicken liver.

Subsequently, dissection of salivary glands was done for extracting their RNA. For this purpose, the first instar larvae were anesthetized on ice and decapitated. Dissection was performed in cold phosphate buffer saline (PBS) with a pH of 7.4 (150 mM NaCl, 10 mM $Na_2HPO_4$). Then salivary glands were dissected 48 hours after feeding a dead mouse body to the first instar *Lucilia sericata* larvae. Therefore six biological replicates, each consisting of salivary glands of three larvae, were collected and frozen on −70° C.

In order to extract RNA for standard reverse transcription PCR (RT-PCR), total RNA was extracted from salivary glands of first instar larvae with total RNA Purification Kit Jena Bioscience Reagent according to the manufacturer's protocol. In addition, genomic DNA contamination was checked by LUF226 (SEQ ID No.3) and R1138 (SEQ ID No. 10) primers after RNA extraction.

Next, the volume of 2 µL of total RNA was adjusted to 20 µL by adding 18 µL RNase-free double distilled water (DDW) and then RNA was incubated at 75° C. for 5 minutes to remove the secondary structures and immediately is placed on ice.

In the second step, for synthesizing cDNA from extracted RNA, reverse transcription (RT) was done by applying gene-specific primer (GSP). More specifically, Accu-Power™ RocketScript™ RT Premix (RevertAid™ Moloney murine leukemia virus [M-MULV] was used as the reverse transcriptase, RNasin as a ribonuclease inhibitor, deoxynucleoside triphosphate (dNTP) solution, an RT buffer, and a primer) was added to the cooled RNA, and reverse transcription was started by the following program: placing RT mixture in a thermal cycler at 25° C. for 10 minutes, then at 42° C. for 60 minutes, and finally at 70° C. for 10 minutes. All of the chemical reagents were obtained from Fermentas™ Company.

In the third step, middle part of the synthesized cDNA of *Lucilia sericata* collagenase was identified as follows. First, since the *Lucilia sericata* genome was not sequenced yet, then, for designing primers, the collagenase RNA sequences of different insects, from highly conserved regions of *M. domestica, T. castaneum, C. quinquefasciatus, B. mori*, and *D. melanogaster*, were aligned by MEGA6 software. After analysis, four regions were chosen for designing the gene-specific primers (GSP) and finally LUF226 (SEQ ID No.3), LUF293 (SEQ ID No.4), LUF353 (SEQ ID No.5), LUF566 (SEQ ID No.6) as forward primers and R1138 (SEQ ID No.10), R1205 (SEQ ID No.11), R1289 (SEQ ID No.12) and R1525 (SEQ ID No.13) as reverse primers were designed for identification of middle part by using Gene Runner, Oligo7, MEGA6, DNASTAR Lasergene™ software.

Then, by applying gene-specific primers to synthesized cDNA, the middle part of the collagenase cDNA was amplified by performing PCR using Analytic Jena thermal cycler. The desired products were amplified by 35 cycles of PCR by using 2 µL of synthesized cDNA in 150 ng/reaction concentration as templates in a reaction containing 2.5 µl PCR buffer, 1 µl forward primer, 1 µl reverse primer, 0.75 µl $MgCl_2$ (1.5 mM), 0.2 µl Taq DNA polymerase, 0.5 µL dNTPs (0.2 mM), and Double Distilled Water (DDW) for adjusting reaction volume to 20 µl.

The PCR program for amplifying middle part of the collagenase cDNA is described as follows. First, the PCR mixture was placed in a thermal cycler at 94° C. for 5 minutes as an initialization step followed by 35 cycles of denaturation DNA templates; then annealing the primers to DNA templates, and then the extension step for synthesizing new DNA strand. The denaturation step was performed by placing the PCR mixture at 94° C. for 30 seconds. Annealing the primers to DNA templates was done at 58° C. for 30 seconds. Extension of middle part of collagenase cDNA was done at 72° C. for 80 seconds. After finishing 35 cycles of the PCR program, in the last cycle, the PCR products, which were the middle part of *Lucilia sericata* collagenase cDNA, were further incubated at 72° C. for 10 minutes to allow the completion of DNA synthesis. The amplified products were purified using DNA gel purification kit (GF-1 Vivantis).

Next, the purified PCR products were cloned into the pTG19-T vector (Vivantis) at molar ratio 3:1 at 22° C. for 40 minutes and then transformed into freshly prepared DH5α strain of *Escherichia coli* (*E. coli*) competent cells. Recombinant clones were selected using blue/white screening on LB agar plates having X-gal (1.6 μg/ml), IPTG (1.6 μg/ml), ampicillin (2 μg/ml). The clones were confirmed by universal M13F and T7promotor primers, and then four recombinant clones (white clones), which have the middle part of cDNA, were picked up for sequencing in both directions. Then, the GeneJET Plasmid Miniprep Kit™ was used to purify the recombinant plasmids, and then the sequence of middle part of collagenase cDNA of *Lucilia sericata* was determined through sequencing.

In the fourth step, identifying 3' end of *Lucilia sericata* collagenase cDNA was carried out by a rapid amplification of cDNA ends (RACE) method. In order to identify 3' end, based on the middle part of the cDNA sequence of *Lucilia sericata* collagenase which was sequenced in the previous step, three oligonucleotides were designed for 3' RACE.

RNA extraction was done using the method explained hereinabove in the first step. Next, for synthesizing cDNA, Linker primer (SEQ ID No.27) was applied as a primer in reverse transcription, and then Outer primer (SEQ ID No.28) and F1359 primer (SEQ ID No.9) were applied for first round of PCR for amplifying 3' end of cDNA of *Lucilia sericata* collagenase.

Afterward, PCR products of first round of PCR were used for second round of PCR. The combination of Inner primer (SEQ ID No.29) (as reverse primer) and F1200 (SEQ ID No.8), F1138 (SEQ ID No.10), and F1146 (SEQ ID No.7) (as forward primers) confirmed the first round in three separate reactions. After the confirmation, the first round PCR products were used for TA cloning into a pTG19-T vector and then the DH5α strain of *E. coli* was transformed with recombinant vectors; then after screening and plasmid extraction, the PCR products of 3' end of collagenase cDNA were sequenced.

In the fifth step, 5' end of *Lucilia sericata* collagenase gene was identified by rapid amplification of genomic ends method (RAGE). At first, after DNA extraction from *Lucilia sericata*, LU5-735 primer (SEQ ID No.26) was used as a primer for making a specific single strand DNA as a template. According to the repeated sequences in promoter region of different organisms, several genome walking primers (GWA (SEQ ID No.14), GWB (SEQ ID No.15), GWC (SEQ ID No.16), GWD (SEQ ID No.17), GWE (SEQ ID No.18), GWF (SEQ ID No.19) and GWG (SEQ ID No.20) were designed for performing PCR and amplifying 5' end of *Lucilia sericata* collagenase gene.

Subsequently, seven micro tubes were labeled and 1 μL of single strand DNA was added to each micro tubes. Then, 1.6 μl of each seven genome walking primers and 3.2 μl of mixed solution (0.4 μl dNTP, 2.2 μl master mix and 0.2 μl Taq DNA polymerase) were added to reactions and PCR was performed by the program reported in TABLE 1. In the last cycle, the PCR products were further incubated at 72° C. for 10 minutes.

Next, ⅕ dilution (volume/volume) of PCR products from the second step was done with double distilled water and diluted PCR products as DNA templates, LU5-377 (SEQ ID No.25) and LU5-243 (SEQ ID No. 23) as reverse primers, and UAP-N1 (SEQ ID No.21) as a forward primer were used in seven separate reactions for seven micro tubes.

Each PCR was performed according to the following PCR program. First, the PCR mixture was placed in a thermal cycler at 94° C. for 5 minutes as an initialization followed by 35 cycles of denaturation DNA templates, annealing the primers to DNA templates, and extension step for synthesizing new DNA strand. The denaturation was performed by placing PCR mixture at 94° C. for 30 seconds; annealing the primers to DNA templates was done at 58° C. for 30 seconds; and extension of new strands which were 5' end of collagenase cDNA was done at 72° C. for 80 seconds. After finishing 35 cycles of the PCR program, in the last cycle, the PCR products were further incubated at 72° C. for 10 minutes to allow the completion of DNA synthesis. The amplified products were purified using DNA gel purification kit (GF-1 Vivantis).

Then, ⅕ dilution (volume/volume) of PCR products of first nested PCR as DNA templates, LU5-317 (SEQ ID No. 24) as reverse primer, and UAP-N2 (SEQ ID No. 22) as forward primer were used in seven separate reactions and each PCR was performed with the same program as previous step. The PCR products of different genome walking primers (GWs) were analyzed on agarose gel 1.5% and products of sharp bands were used in TA cloning and 5' end of cDNA of *Lucilia sericata* collagenase was sequenced as explained in previous steps.

In the sixth step, full length of *Lucilia sericata* collagenase cDNA and its gene were identified based on the identification of the middle part and 3' end of *Lucilia sericata* cDNA and 5'end of *Lucilia sericata* collagenase gene. The different known fragments were assembled by DNA Laser gene7 software. Therefore, the assembled sequence was considered as full length cDNA sequence of collagenase (MMP1) of *Lucilia sericata*. Then F1 primer (SEQ ID No.30) as forward primer and R1177 (SEQ ID No.31) as reverse primer were designed to amplify the CDS of cDNA and open reading frame (ORF) of *Lucilia sericata* collagenase gene for identifying full length sequence of collagenase cDNA and gene.

After that, the RNA extraction from salivary glands of *Lucilia sericata* was again performed as explained in the first step. cDNA synthesis was done by using oligo dT primer and through a procedure described in the second step. DNA extraction was carried out from *Lucilia sericata* salivary glands. Then PCR reaction was performed using F1 (SEQ ID No.30) as a forward primer and R1177 (SEQ ID No.31) as a reverse primer and according to the following PCR program. First, the PCR mixture was placed in a thermal cycler at 94° C. for 5 minutes as an initialization followed by 35 cycles of denaturation DNA templates, then annealing the primers to DNA templates, and extension step for synthesizing new DNA strand. The denaturation step was performed by placing PCR mixture at 94° C. for 30 seconds; annealing the primers to DNA templates was done at 58° C. for 40 seconds; and extension of full lengths of collagenase cDNA and gene was done at 72° C. for 80 seconds. In the last cycle, the PCR products were further incubated at 72° C. for 10 minutes.

Then the PCR products of this step were cloned into pTG19-T vector and after screening and plasmid extraction, the full length of cDNA *Lucilia sericata* collagenase (SEQ ID No. 1) and *Lucilia sericata* collagenase gene (SEQ ID No.32) was determined by sequencing the recombinant plasmids.

Comparison between collagenase gene and cDNA of *Lucilia sericata* shows that the collagenase gene of *Lucilia sericata* contains three exons and two introns and the first intron starts from nucleotide number 398 to nucleotide number 463 and the secondary intron starts form nucleotide number 1022 to nucleotide number 1090. Also the coding sequence of cDNA has 1212 nucleotides and starts from nucleotide number 493 to amino acid number 1704.

Example 2: Characterization of *Lucilia sericata* Collagenase

Based on *Lucilia sericata* collagenase cDNA sequence (SEQ ID No.1) which has a coding sequence of 1212 nucleotides, the amino acid sequence of *Lucilia sericata* collagenase (SEQ ID No.2) was predicted and characterized. The deduced amino acid sequence of *Lucilia sericata* collagenase consists of 404 amino acid residues and has a calculated molecular mass of about 45109.8 Dalton.

Also the amino acid composition in *Lucilia sericata* collagenase includes Alanine (A) 7.9%, Arginine (R) 5.2%, Asparagine (N) 3.7%, Aspartate (D) 7.7%, Cysteine (C) 0.5%, Glutamine (Q) 2.0%, Glutamate (E) 3.5%, Glycine (G) 10.1%, Histidine (H) 2.0%, Isoleucine (I) 3.7%, Leucine (L) 6.7%, Lysine (K) 7.9%, Methionine (M) 1.2%, Phenylalanine (F) 6.9%, Proline (P) 6.7%, Serine (S) 7.7%, Threonine (T) 4.5%, Tryptophan (W) 2.0%, Tyrosine (Y) 5.7% and Valine (V) 4.5%.

Comparison of the predicted amino acid sequence to those of the vertebrate and insect MMPs demonstrated that the *Lucilia sericata* has all of the typical structural features of MMPs family members. The presence of hydrophobic residues stretch close to the proposed initiator methionine suggests the presence of the signal sequence (amino acids 7 to 13), which is the characteristic of most MMPs.

Using BLAST (basic local alignment search tool) for nucleotide sequence and protein analysis revealed that *Lucilia sericata* collagenase is similar to the insect and vertebrate MMPs, particularly to MMP 14 of *M. domestica*; because *Lucilia sericata* cDNA and protein sequences shares 83% and 92% homology to MMP 14 of *M. domestica* respectively.

Figure 3:
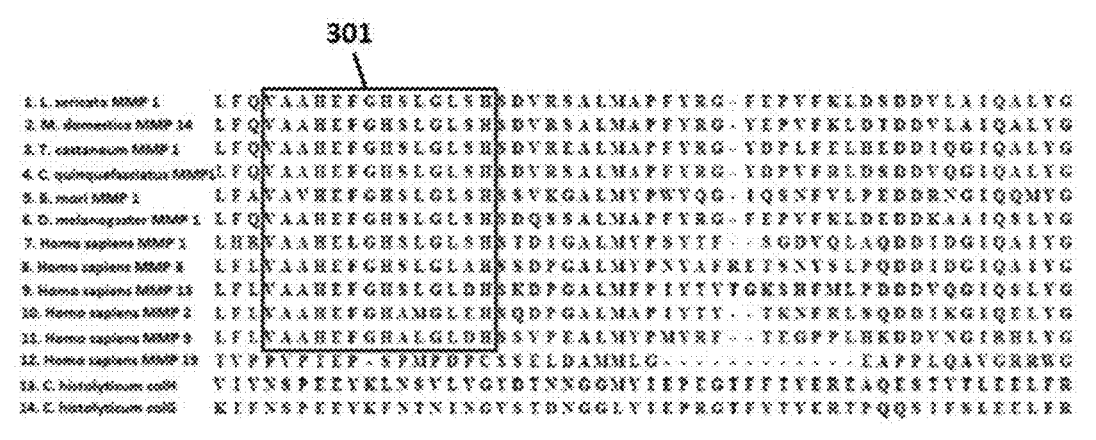

Referring to FIG. 3, the identity of predicted *Lucilia sericata* collagenase was further confirmed by aligning the amino acid sequences of conserved regions involved in substrate specificity and activity of Zinc-peptidases MMPs for *Lucilia sericata* collagenase (MMP1) against MMPs sequences from fourteen organisms of insects, mammalian and bacteria. The conserved region shown in the box 301 is Zinc-binding consensus sequence "VAAHEXX-HXXGXXHS" as set forth in SEQ ID NO. 33 which is the characteristic feature of the Metzincin super family of Zinc-peptidases. Alignment of the amino acid sequences of different MMPs was performed using MEGA6 ClustalW multiple sequence alignment.

Due to a wide range of functional and structural roles of the Zinc ions, identification of the Zinc-binding sites was also done by Zinc Explorer software. The Zinc-binding site of collagenase is predicted to consist of Cys9, His92, Asp94, His141, His145 and His151. Collagenase of *Lucilia sericata* also has a sequence PRCGVXD amino acid residue 7 to amino acid residue 17 of SEQ ID NO. 2 which is a conserved motif in the prodomain of MMPs and it is involved in maintenance of latency phase MMPs also contain a C-terminal hemopexin-like domain which proposed to play an essential role in the structure of the active sites of these enzymes. Hemopexin is a heme-binding protein that transports heme to the liver. Also, C-terminal Hemopexin-like domain of *Lucilia sericata* collagenase has about 200 amino acid residues.

Figure 4A:
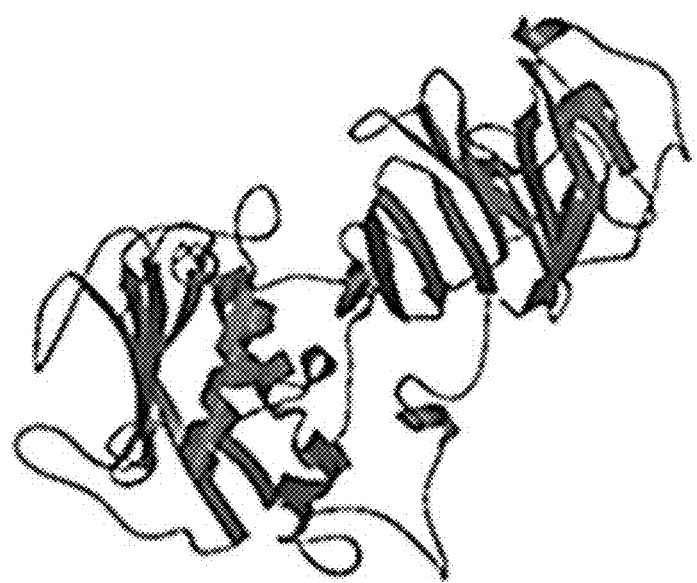
FIG. 4A shows a three-dimensional structure of *Lucilia sericata* collagenase
Figure 4B:
FIG. 4B shows a three-dimensional structure of *Homo sapiens* MMP 2.

FIG. 4 illustrates the comparison between three-dimensional structures of *Lucilia sericata* collagenase MMP 1 (A) and human MMP 2 (B). The three-dimensional structure of *Lucilia sericata* collagenase was predicted by using Phyre web server and compared to the three-dimensional structure of human MMP 13. Based on their high similarity in critical domains, their structures and three-dimensional conformations (alpha helices and beta sheets) were very similar, especially in the substrate-binding pocket and the active site.

Figure 5:
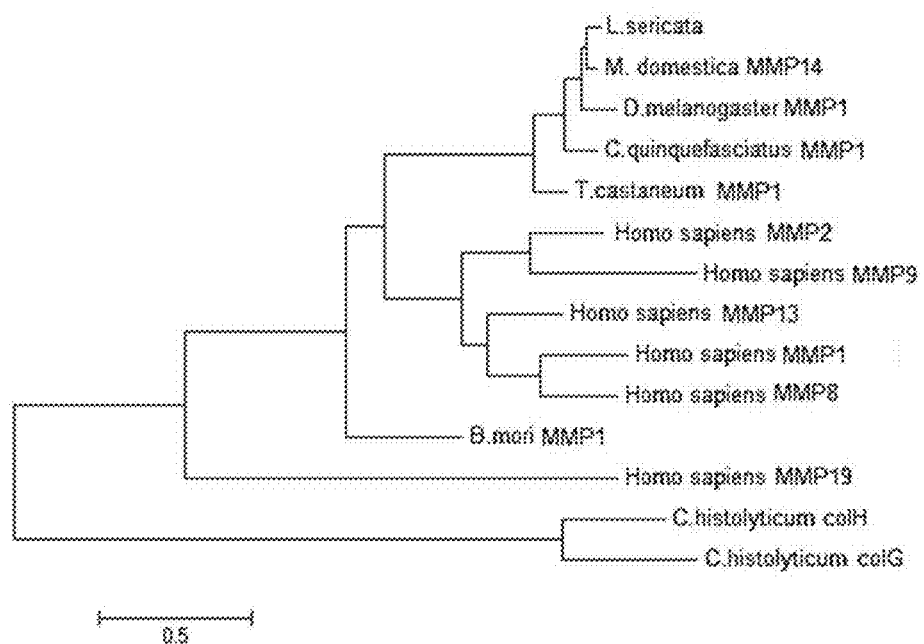
FIG. 5 shows a phylogenetic tree of *Lucilia sericata* collagenase (MMP1) and several amino acid sequences of MMPs.

FIG. 5 shows a phylogenetic tree that was built based on amino acid sequence homology between *Lucilia sericata* collagenase (MMP1) and thirteen MMP sequences from different organisms, for example, mammalian and bacteria. The difference between branches' length indicates the genetic changes between different sequences; so the sequences can be classified based on their homology.

Referring to FIG. 5, the phylogenetic tree illustrates that predicted sequence of *Lucilia sericata* collagenase (MMP 1) is very similar to insect's MMPs such as *M. domestica* MMP 14, *D. melanogaster* MMP 1, *C. quinquefasciatus* MMP 1, and *T. castaneum* MMP 1, and also similar to the mammalian MMPs such as *Homo sapiens* MMP 1, MMP 8, MMP 13, MMP 2, MMP 9, MMP 19 while this phylogenetic tree shows that predicted sequence of *Lucilia sericata* collagenase (MMP 1) is highly different from bacterial collagenases like *C. histolyticum* colH and colG. The low homology between insects and human MMPs with bacterial collagenases is because of the fact that the Zinc-binding domains in bacterial MMPs like colH and colG are totally different from other organism's Zinc-binding domains.

What is claimed is:

1. A complementary DNA (cDNA), wherein the cDNA comprises SEQ ID NO: 1 and encodes a collagenase enzyme of *Lucilia sericata*.

2. The cDNA according to claim 1, wherein the cDNA encodes a collagenase enzyme of *Lucilia sericata* with a molecular weight of 45.1 kilodaltons (kDa).

3. The cDNA according to claim 1, wherein the cDNA is identified by a method comprising:

extracting RNA from salivary glands of *Lucilia sericata*;

synthesizing the cDNA from extracted RNA;

identifying a middle part of the cDNA sequence of *Lucilia sericata* collagenase;

identifying a 3' end of the cDNA sequence of *Lucilia sericata* collagenase through a rapid amplification of cDNA ends technique (RACE);

identifying a 5' end of the cDNA sequence of *Lucilia sericata* collagenase gene through a rapid amplification of genomic ends technique (RAGE); and identifying a full-length cDNA sequence of *Lucilia sericata* collagenase, the full-length cDNA sequence being as set forth in SEQ ID NO: 1.

* * * * *

SEQUENCE LISTING

```
<160> NUMBER OF SEQ ID NOS: 47

<210> SEQ ID NO 1
<211> LENGTH: 1932
<212> TYPE: DNA
<213> ORGANISM: Lucilia sericata
<220> FEATURE:
<221> NAME/KEY: misc_feature
<222> LOCATION: (222)..(396)
<223> OTHER INFORMATION: Hemopexin-like domain
<220> FEATURE:
<221> NAME/KEY: CDS
<222> LOCATION: (493)..(1704)

<400> SEQUENCE: 1
agctacttat cttgtttatg atttatccca gatttcttct cgatacacat gcgttcggga      60
```

-continued

```
atatctgaac gaatgtgatg cttacttta tcgttaaata tcggacagtt acagaatagg    120
tcctcctcat taaaataact tctgctttag tttttgtatt cgagatcttt cttcaatagg    180
aattacctaa gtaacggtct ctattctagg taaatgtcgg atagtagtgg ggtatatggg    240
acactatctc ctcttaatct taattaaggc aacttttgaa gaagttatta tattcaatat    300
caagtcttct ggtagtggta gctatgacac agtgtttact gataaagcag tcttatctat    360
tgtctacgaa agcttgacct aagcgaggtc ttacatgtga tttcattaaa ccagctgagt    420
tgggctcaaa gctgtgcagg actttcaaag ttttgccggt ttaaatacca ccggtgagct    480
agatgctgag ac atg gaa tta atg tca ctg cca cgt tgt ggt gta cgc gat  531
              Met Glu Leu Met Ser Leu Pro Arg Cys Gly Val Arg Asp
              1               5                  10 aag gtg ggc ttt ggt aat gat aat cgt tcc aag cgt tat gca ctc cag    579
Lys Val Gly Phe Gly Asn Asp Asn Arg Ser Lys Arg Tyr Ala Leu Gln
     15                 20                  25 ggc agc cgt tgg cgt gta aag gct ttg acc tat aaa atc tcc aaa tat    627
Gly Ser Arg Trp Arg Val Lys Ala Leu Thr Tyr Lys Ile Ser Lys Tyr
30                  35                  40                  45 cct aaa cgt ttg aag aaa gct gat gtt gat gcc gaa att gca aga gct    675
Pro Lys Arg Leu Lys Lys Ala Asp Val Asp Ala Glu Ile Ala Arg Ala
                 50                  55                  60 ttt gct gtc tgg agc gaa tac acc gat cta agt ttt aca ccc aaa agt    723
Phe Ala Val Trp Ser Glu Tyr Thr Asp Leu Ser Phe Thr Pro Lys Ser
             65                  70                  75 tcg gga cca gta cat att gaa att aaa ttt gtt gaa agt gaa cat ggt    771
Ser Gly Pro Val His Ile Glu Ile Lys Phe Val Glu Ser Glu His Gly
         80                  85                  90 gat ggt gac gct ttc gat ggt gta ggt ggc acc ttg gct cat gcc ttc    819
Asp Gly Asp Ala Phe Asp Gly Val Gly Gly Thr Leu Ala His Ala Phe
     95                  100                 105 ttc cct gtc ttt ggt ggt gat gct cat ttt gat gat gct gaa ctt tgg    867
Phe Pro Val Phe Gly Gly Asp Ala His Phe Asp Asp Ala Glu Leu Trp
110                 115                 120                 125 acc att ggc agt cct cgt ggc act aat ctt ttc caa gta gct gct cat    915
Thr Ile Gly Ser Pro Arg Gly Thr Asn Leu Phe Gln Val Ala Ala His
                 130                 135                 140 gaa ttt ggt cac tct ttg ggt ttg tca cat tcc gat gta cgt tcc gct    963
Glu Phe Gly His Ser Leu Gly Leu Ser His Ser Asp Val Arg Ser Ala
             145                 150                 155 cta atg gct ccc ttc tat cgt ggt ttt gag cct gtt ttc aaa ttg gac   1011
Leu Met Ala Pro Phe Tyr Arg Gly Phe Glu Pro Val Phe Lys Leu Asp
         160                 165                 170 tct gat gat gtt tta gcc att cag gct tta tat ggc aag aag tcc tct   1059
Ser Asp Asp Val Leu Ala Ile Gln Ala Leu Tyr Gly Lys Lys Ser Ser
     175                 180                 185 tca aat ggt aat ggt ata aat ccc ccc agc ggt ggt gcc ttc cca cgt   1107
Ser Asn Gly Asn Gly Ile Asn Pro Pro Ser Gly Gly Ala Phe Pro Arg
190                 195                 200                 205 acc aca caa aga ccc gcc ttt gct cca cca cgc aca ccc aga gat gat   1155
Thr Thr Gln Arg Pro Ala Phe Ala Pro Pro Arg Thr Pro Arg Asp Asp
                 210                 215                 220 caa tta tgt aaa gat ccc aaa att gat gct ctc ttc aac tca gcc gat   1203
Gln Leu Cys Lys Asp Pro Lys Ile Asp Ala Leu Phe Asn Ser Ala Asp
             225                 230                 235 ggc cag act tat gct ctt aag ggc aat aaa tac tat aag ctt acc gaa   1251
Gly Gln Thr Tyr Ala Leu Lys Gly Asn Lys Tyr Tyr Lys Leu Thr Glu
         240                 245                 250 aac tca gtg gcc gac gga tat ccc aaa ctt atc tca gaa gga tgg cct   1299
```

```
                Asn Ser Val Ala Asp Gly Tyr Pro Lys Leu Ile Ser Glu Gly Trp Pro
                    255                 260                 265 gtt tta cca ggc gat att gat gct gct ttt acc tat aaa agt ggc aaa       1347
Gly Leu Pro Gly Asp Ile Asp Ala Ala Phe Thr Tyr Lys Ser Gly Lys
270                 275                 280                 285 aca tat ttc ttc aag ggc acc aaa tat tgg cgt tat aat ggc cgt caa       1395
Thr Tyr Phe Phe Lys Gly Thr Lys Tyr Trp Arg Tyr Asn Gly Arg Gln
                290                 295                 300 atg gat ggt gat tac ccg aaa gag att agt gaa ggt ttt act gga gtg       1443
Met Asp Gly Asp Tyr Pro Lys Glu Ile Ser Glu Gly Phe Thr Gly Val
            305                 310                 315 ccc gat cat ttg gat gct gcc atg gtt tgg ggc ggt aat ggt aaa att       1491
Pro Asp His Leu Asp Ala Ala Met Val Trp Gly Gly Asn Gly Lys Ile
        320                 325                 330 tac ttc tat aag ggc agt aaa ttc tgg cgt ttc gat ccc ttg aag aga       1539
Tyr Phe Tyr Lys Gly Ser Lys Phe Trp Arg Phe Asp Pro Leu Lys Arg
    335                 340                 345 cca cca gtt aag tcc agc tat ccc ttc tgg cgt ttc gat ccc ttg aag       1587
Pro Pro Val Lys Ser Ser Tyr Pro Phe Trp Arg Phe Asp Pro Leu Lys
350                 355                 360                 365 aga cca cca gtt aag tcc agc tat ccc caa tat acc aat ggt tat acg       1635
Arg Pro Pro Val Lys Ser Ser Tyr Pro Gln Tyr Thr Asn Gly Tyr Thr
                370                 375                 380 tac ttc ttt aag ggt gat aaa tac tat cgg ttt aac gat aga aca ttt       1683
Tyr Phe Phe Lys Gly Asp Lys Tyr Tyr Arg Phe Asn Asp Arg Thr Phe
            385                 390                 395 gca gta agt att tct ctg ata tgaatatgtg aaagcttgtt attttttaaa         1734
Ala Val Ser Ile Ser Leu Ile
        400 gctttcaaag agcttttta acaagctttt acgaagtaga tattcttaaa aaaaactttt      1794 taaagaagat acatatatgg aatatagtat taaaaatagc tttcaagaag aattttaaaa     1854 agcttttagt ttgaaaaacc agttatacaa agcttttttt aattaggctt taaagctgtt    1914 ttataaaaaa aaaaaaaa                                                   1932

<210> SEQ ID NO 2
<211> LENGTH: 404
<212> TYPE: PRT
<213> ORGANISM: Lucilia sericata

<400> SEQUENCE: 2

Met Glu Leu Met Ser Leu Pro Arg Cys Gly Val Arg Asp Lys Val Gly
1               5                   10                  15

Phe Gly Asn Asp Asn Arg Ser Lys Arg Tyr Ala Leu Gln Gly Ser Arg
            20                  25                  30

Trp Arg Val Lys Ala Leu Thr Tyr Lys Ile Ser Lys Tyr Pro Lys Arg
        35                  40                  45

Leu Lys Lys Ala Asp Val Asp Ala Glu Ile Ala Arg Ala Phe Ala Val
    50                  55                  60

Trp Ser Glu Tyr Thr Asp Leu Ser Phe Thr Pro Lys Ser Ser Gly Pro
65                  70                  75                  80

Val His Ile Glu Ile Lys Phe Val Glu Ser Glu His Gly Asp Gly Asp
                85                  90                  95

Ala Phe Asp Gly Val Gly Gly Thr Leu Ala His Ala Phe Phe Pro Val
            100                 105                 110

Phe Gly Gly Asp Ala His Phe Asp Asp Ala Glu Leu Trp Thr Ile Gly
        115                 120                 125
```

```
Ser Pro Arg Gly Thr Asn Leu Phe Gln Val Ala Ala His Glu Phe Gly
    130                 135                 140
His Ser Leu Gly Leu Ser His Ser Asp Val Arg Ser Ala Leu Met Ala
145                 150                 155                 160
Pro Phe Tyr Arg Gly Phe Glu Pro Val Phe Lys Leu Asp Ser Asp Asp
                165                 170                 175
Val Leu Ala Ile Gln Ala Leu Tyr Gly Lys Lys Ser Ser Ser Asn Gly
            180                 185                 190
Asn Gly Ile Asn Pro Pro Ser Gly Gly Ala Phe Pro Arg Thr Thr Gln
        195                 200                 205
Arg Pro Ala Phe Ala Pro Pro Arg Thr Pro Arg Asp Asp Gln Leu Cys
    210                 215                 220
Lys Asp Pro Lys Ile Asp Ala Leu Phe Asn Ser Ala Asp Gly Gln Thr
225                 230                 235                 240
Tyr Ala Leu Lys Gly Asn Lys Tyr Tyr Lys Leu Thr Glu Asn Ser Val
                245                 250                 255
Ala Asp Gly Tyr Pro Lys Leu Ile Ser Glu Gly Trp Pro Gly Leu Pro
            260                 265                 270
Gly Asp Ile Asp Ala Ala Phe Thr Tyr Lys Ser Gly Lys Thr Tyr Phe
        275                 280                 285
Phe Lys Gly Thr Lys Tyr Trp Arg Tyr Asn Gly Arg Gln Met Asp Gly
    290                 295                 300
Asp Tyr Pro Lys Glu Ile Ser Glu Gly Phe Thr Gly Val Pro Asp His
305                 310                 315                 320
Leu Asp Ala Ala Met Val Trp Gly Gly Asn Gly Lys Ile Tyr Phe Tyr
                325                 330                 335
Lys Gly Ser Lys Phe Trp Arg Phe Asp Pro Leu Lys Arg Pro Pro Val
            340                 345                 350
Lys Ser Ser Tyr Pro Phe Trp Arg Phe Asp Pro Leu Lys Arg Pro Pro
        355                 360                 365
Val Lys Ser Ser Tyr Pro Gln Tyr Thr Asn Gly Tyr Thr Tyr Phe Phe
    370                 375                 380
Lys Gly Asp Lys Tyr Tyr Arg Phe Asn Asp Arg Thr Phe Ala Val Ser
385                 390                 395                 400
Ile Ser Leu Ile

<210> SEQ ID NO 3
<211> LENGTH: 21
<212> TYPE: DNA
<213> ORGANISM: Artificial Sequence
<220> FEATURE:
<223> OTHER INFORMATION: synthetic sequence

<400> SEQUENCE: 3
agccgtgcag gactttcaaa g                                           21

<210> SEQ ID NO 4
<211> LENGTH: 25
<212> TYPE: DNA
<213> ORGANISM: Artificial Sequence
<220> FEATURE:
<223> OTHER INFORMATION: Primer sequence

<400> SEQUENCE: 4
gaattaatgt cactgccacg ttgtg                                       25

<210> SEQ ID NO 5
```

```
<211> LENGTH: 24
<212> TYPE: DNA
<213> ORGANISM: Artificial Sequence
<220> FEATURE:
<223> OTHER INFORMATION: Primer Sequence

<400> SEQUENCE: 5
cgttctaagc gttatgcact ccag                                              24

<210> SEQ ID NO 6
<211> LENGTH: 22
<212> TYPE: DNA
<213> ORGANISM: Artificial Sequence
<220> FEATURE:
<223> OTHER INFORMATION: Primer sequence

<400> SEQUENCE: 6
ggtgatggtg acgctttcga tg                                                22

<210> SEQ ID NO 7
<211> LENGTH: 28
<212> TYPE: DNA
<213> ORGANISM: Artificial Sequence
<220> FEATURE:
<223> OTHER INFORMATION: Primer sequence

<400> SEQUENCE: 7
catatttctt caagggcacc aaatattg                                          28

<210> SEQ ID NO 8
<211> LENGTH: 27
<212> TYPE: DNA
<213> ORGANISM: Artificial Sequence
<220> FEATURE:
<223> OTHER INFORMATION: Primer sequence

<400> SEQUENCE: 8
gtgattaccc gaaagagatt agtgaag                                           27

<210> SEQ ID NO 9
<211> LENGTH: 24
<212> TYPE: DNA
<213> ORGANISM: Artificial Sequence
<220> FEATURE:
<223> OTHER INFORMATION: Primer sequence

<400> SEQUENCE: 9
ccaaaccgat ttcgaattgg gaag                                              24

<210> SEQ ID NO 10
<211> LENGTH: 26
<212> TYPE: DNA
<213> ORGANISM: Artificial Sequence
<220> FEATURE:
<223> OTHER INFORMATION: Primer sequence

<400> SEQUENCE: 10
tgcccttgaa gaaatatgtt ttgcca                                            26

<210> SEQ ID NO 11
<211> LENGTH: 29
<212> TYPE: DNA
<213> ORGANISM: Artificial Sequence
<220> FEATURE:
<223> OTHER INFORMATION: Primer sequence

<400> SEQUENCE: 11
```
gtaaaacctt cactaatctc tttcgggta                                          29

<210> SEQ ID NO 12
<211> LENGTH: 28
<212> TYPE: DNA
<213> ORGANISM: Artificial Sequence
<220> FEATURE:
<223> OTHER INFORMATION: Primer sequence

<400> SEQUENCE: 12
gccagaattt actgcccetta tagaagta                                          28

<210> SEQ ID NO 13
<211> LENGTH: 20
<212> TYPE: DNA
<213> ORGANISM: Artificial Sequence
<220> FEATURE:
<223> OTHER INFORMATION: Primer Sequence

<400> SEQUENCE: 13
tcttgcaacc gaaccaccag                                                    20

<210> SEQ ID NO 14
<211> LENGTH: 28
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (21)..(22)
<223> OTHER INFORMATION: can be any nucleotide

<400> SEQUENCE: 14
gatcaggcgt cgcgtacctc nnctactg                                           28

<210> SEQ ID NO 15
<211> LENGTH: 27
<212> TYPE: DNA
<213> ORGANISM: Artificial Sequence
<220> FEATURE:
<223> OTHER INFORMATION: Primer Sequence
<220> FEATURE:
<221> NAME/KEY: misc_feature
<222> LOCATION: (21)..(22)
<223> OTHER INFORMATION: can be any nucleotide

<400> SEQUENCE: 15
gatcaggcgt cgcgtacctc nnctact                                            27

<210> SEQ ID NO 16
<211> LENGTH: 26
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
<222> LOCATION: (21)..(22)
<223> OTHER INFORMATION: can be any nucleotide

<400> SEQUENCE: 16
gatcaggcgt cgcgtacctc nnctac                                             26

<210> SEQ ID NO 17
<211> LENGTH: 28
<212> TYPE: DNA

```
<213> ORGANISM: Artificial Sequence
<220> FEATURE:
<223> OTHER INFORMATION: Primer sequence
<220> FEATURE:
<221> NAME/KEY: misc_feature
<222> LOCATION: (21)..(22)
<223> OTHER INFORMATION: can be any nucleotide

<400> SEQUENCE: 17
gatcaggcgt cgcgtacctc nncacgca                                              28

<210> SEQ ID NO 18
<211> LENGTH: 27
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
<222> LOCATION: (21)..(22)
<223> OTHER INFORMATION: can be any nucleotide

<400> SEQUENCE: 18
gatcaggcgt cgcgtacctc nncacgc                                               27

<210> SEQ ID NO 19
<211> LENGTH: 26
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
<222> LOCATION: (21)..(22)
<223> OTHER INFORMATION: can be any nucleotide

<400> SEQUENCE: 19
gatcaggcgt cgcgtacctc nncacg                                                26

<210> SEQ ID NO 20
<211> LENGTH: 27
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
<222> LOCATION: (21)..(22)
<223> OTHER INFORMATION: can be any nucleotide

<400> SEQUENCE: 20
gatcaggcgt cgcgtacctc nngagac                                               27

<210> SEQ ID NO 21
<211> LENGTH: 42
<212> TYPE: DNA
<213> ORGANISM: Artificial Sequence
<220> FEATURE:
<223> OTHER INFORMATION: Primer sequence

<400> SEQUENCE: 21
cctgtgagca gtcgtatcca ccgatcaggc gtcgcgtacc tc                              42

<210> SEQ ID NO 22
<211> LENGTH: 21
<212> TYPE: DNA
<213> ORGANISM: Artificial Sequence
<220> FEATURE:
<223> OTHER INFORMATION: Primer sequence
```

```
<400> SEQUENCE: 22
cctgtgagca gtcgtatcca c                                              21

<210> SEQ ID NO 23
<211> LENGTH: 21
<212> TYPE: DNA
<213> ORGANISM: Artificial Sequence
<220> FEATURE:
<223> OTHER INFORMATION: Primer sequence

<400> SEQUENCE: 23
tgaaagtcct gcacggcttt g                                              21

<210> SEQ ID NO 24
<211> LENGTH: 25
<212> TYPE: DNA
<213> ORGANISM: Artificial Sequence
<220> FEATURE:
<223> OTHER INFORMATION: synthetic sequence

<400> SEQUENCE: 24
cacaacgtgg cagtgacatt aattc                                          25

<210> SEQ ID NO 25
<211> LENGTH: 24
<212> TYPE: DNA
<213> ORGANISM: Artificial Sequence
<220> FEATURE:
<223> OTHER INFORMATION: synthetic sequence

<400> SEQUENCE: 25
cctggagtgc ataacgctta gaac                                           24

<210> SEQ ID NO 26
<211> LENGTH: 26
<212> TYPE: DNA
<213> ORGANISM: Artificial Sequence
<220> FEATURE:
<223> OTHER INFORMATION: synthetic sequence

<400> SEQUENCE: 26
aaacccaaag agtgaccaaa ttcatg                                         26

<210> SEQ ID NO 27
<211> LENGTH: 41
<212> TYPE: DNA
<213> ORGANISM: Artificial Sequence
<220> FEATURE:
<223> OTHER INFORMATION: Synthetic primer

<400> SEQUENCE: 27
gcgagcacag aattaatacg actctttttt tttttttttt t                        41

<210> SEQ ID NO 28
<211> LENGTH: 24
<212> TYPE: DNA
<213> ORGANISM: Artificial Sequence
<220> FEATURE:
<223> OTHER INFORMATION: synthetic sequence

<400> SEQUENCE: 28
gcgagcacag aattaatacg actc                                           24

<210> SEQ ID NO 29
```

-continued

```
<211> LENGTH: 28
<212> TYPE: DNA
<213> ORGANISM: Artificial Sequence
<220> FEATURE:
<223> OTHER INFORMATION: Primer

<400> SEQUENCE: 29
gcacagaatt aatacgactc actatagg                                        28

<210> SEQ ID NO 30
<211> LENGTH: 25
<212> TYPE: DNA
<213> ORGANISM: Artificial Sequence
<220> FEATURE:
<223> OTHER INFORMATION: primer

<400> SEQUENCE: 30
atggcaatta atgtcactgc cacgt                                           25

<210> SEQ ID NO 31
<211> LENGTH: 37
<212> TYPE: DNA
<213> ORGANISM: Artificial Sequence
<220> FEATURE:
<223> OTHER INFORMATION: Artificial Primer

<400> SEQUENCE: 31
tatcagagaa atactatact gcaaatgttc tatcgtt                              37

<210> SEQ ID NO 32
<211> LENGTH: 1351
<212> TYPE: DNA
<213> ORGANISM: Lucilia sericata
<220> FEATURE:
<221> NAME/KEY: Intron
<222> LOCATION: (398)..(463)
<220> FEATURE:
<221> NAME/KEY: Intron
<222> LOCATION: (1022)..(1090)

<400> SEQUENCE: 32
tatcagagaa atacttactg caaatgttct atcgttaaac cgatagtatt tatcacccctt     60 aaagaagtac gtataaccat tggtatattg taaggcagca tctaaactat ttggcaagcc    120
ttcccaattc gaaatcggtt tgggatagct ggacttaact ggtggtctct tcaagggatc    180
gaaacgccag aatttactgc ccttatagaa gtaaatttta ccattaccgc cccaaaccat    240
ggcagcatcc aaatgatcgg gcactccagt aaaaccttca ctaatctctt tcgggtaatc    300
accatccatt tgacggccat tataacgcca atatttggtg cccttgaaga aatatgtttt    360
gccactttta taggtaaaag cagcatcaat atcgcctaaa gttgaatgaa aaagaaatcg    420
ttaaaatagt tcaagaagtt aagaggaagt ctaacaccca cctggtaaac caggccatcc    480
ttctgagata agtttgggat atccgtcggc cactgagttt tcggtaagct tatagtattt    540
attgccctta agagcataag tctggccatc ggctgagttg aagagagcat caattttggg    600
atctttacat aattgatcat ctctgggtgt gcgtggtgga gcaaaggcgg gtctttgtgt    660
ggtacgtggg aaggcaccac cgctgggggg atttatacca ttaccatttg aagaggactt    720
cttgccatat aaagcctgaa tggctaaaac atcatcagag tccatttgaa aacaggctc    780 aaaaccacga tagaagggag ccattagagc ggaacgtaca tcggaatgtg acaaacccaa    840
agagtgacca aattcatgag cagctacttg gaaaagatta gtgccacgag gactgccaat    900
ggtccaaagt tcagcatcat caaaatgagc atcaccacca aagacaggga agaaggcatg    960
```

```
agccaaggtg ccacctacac catcgaaagc gtcaccatca ccatgttcac tttcaacaaa    1020
tctgtaaaaa attttaagaa ttttaattaa taaacaaact ttctttcttt tttagtttcc    1080
caaaacttac ttaatttcaa tatgtactgg tcccgaactt ttgggtgtaa aacttagatc    1140
ggtgttattc gcgcctccag acagcaaaag ctctagcaat ttcggcatca acatcagctt    1200
tcttcaaacg tttaggatat ttggagattt tataggtcaa agcctttaca cgccaacggc    1260
tgccctggag tgcataacgc ttggaacgat tatcattacc aaagcccacc ttatcgcgta    1320
caccacaacg tggcagtgac attaattcca t                                   1351
```

<210> SEQ ID NO 33
<211> LENGTH: 15
<212> TYPE: PRT
<213> ORGANISM: Artificial Sequence
<220> FEATURE:
<223> OTHER INFORMATION: consensus sequence
<220> FEATURE:
<221> NAME/KEY: misc_feature
<222> LOCATION: (6)..(7)
<223> OTHER INFORMATION: Xaa can be any naturally occurring amino acid
<220> FEATURE:
<221> NAME/KEY: misc_feature
<222> LOCATION: (9)..(10)
<223> OTHER INFORMATION: Xaa can be any naturally occurring amino acid
<220> FEATURE:
<221> NAME/KEY: misc_feature
<222> LOCATION: (12)..(13)
<223> OTHER INFORMATION: Xaa can be any naturally occurring amino acid

<400> SEQUENCE: 33

Val Ala Ala His Glu Xaa Xaa His Xaa Xaa Gly Xaa Xaa His Ser
1               5                   10                  15

<210> SEQ ID NO 34
<211> LENGTH: 404
<212> TYPE: PRT
<213> ORGANISM: Lucilia sericata

<400> SEQUENCE: 34

Met Glu Leu Met Ser Leu Pro Arg Cys Gly Val Arg Asp Lys Val Gly
1               5                   10                  15

Phe Gly Asn Asp Asn Arg Ser Lys Arg Tyr Ala Leu Gln Gly Ser Arg
            20                  25                  30

Trp Arg Val Lys Ala Leu Thr Tyr Lys Ile Ser Lys Tyr Pro Lys Arg
        35                  40                  45

Leu Lys Lys Ala Asp Val Asp Ala Glu Ile Ala Arg Ala Phe Ala Val
    50                  55                  60

Trp Ser Glu Tyr Thr Asp Leu Ser Phe Thr Pro Lys Ser Ser Gly Pro
65                  70                  75                  80

Val His Ile Glu Ile Lys Phe Val Glu Ser Glu His Gly Asp Gly Asp
                85                  90                  95

Ala Phe Asp Gly Val Gly Gly Thr Leu Ala His Ala Phe Phe Pro Val
            100                 105                 110

Phe Gly Gly Asp Ala His Phe Asp Asp Ala Glu Leu Trp Thr Ile Gly
        115                 120                 125

Ser Pro Arg Gly Thr Asn Leu Phe Gln Val Ala Ala His Glu Phe Gly
    130                 135                 140

His Ser Leu Gly Leu Ser His Ser Asp Val Arg Ser Ala Leu Met Ala
145                 150                 155                 160

Pro Phe Tyr Arg Gly Phe Glu Pro Val Phe Lys Leu Asp Ser Asp Asp

```
                165                 170                 175
Val Leu Ala Ile Gln Ala Leu Tyr Gly Lys Ser Ser Asn Gly
            180                 185                 190

Asn Gly Ile Asn Pro Pro Ser Gly Ala Phe Pro Arg Thr Thr Gln
            195                 200                 205

Arg Pro Ala Phe Ala Pro Arg Thr Pro Arg Asp Asp Gln Leu Cys
        210                 215                 220

Lys Asp Pro Lys Ile Asp Ala Leu Phe Asn Ser Ala Asp Gly Gln Thr
225                 230                 235                 240

Tyr Ala Leu Lys Gly Asn Lys Tyr Tyr Lys Leu Thr Glu Asn Ser Val
                245                 250                 255

Ala Asp Gly Tyr Pro Lys Leu Ile Ser Glu Gly Trp Pro Gly Leu Pro
                260                 265                 270

Gly Asp Ile Asp Ala Ala Phe Thr Tyr Lys Ser Gly Lys Thr Tyr Phe
                275                 280                 285

Phe Lys Gly Thr Lys Tyr Trp Arg Tyr Asn Gly Arg Gln Met Asp Gly
            290                 295                 300

Asp Tyr Pro Lys Glu Ile Ser Glu Gly Phe Thr Gly Val Pro Asp His
305                 310                 315                 320

Leu Asp Ala Ala Met Val Trp Gly Gly Asn Gly Lys Ile Tyr Phe Tyr
                325                 330                 335

Lys Gly Ser Lys Phe Trp Arg Phe Asp Pro Leu Lys Arg Pro Pro Val
            340                 345                 350

Lys Ser Ser Tyr Pro Lys Pro Ile Ser Asn Trp Glu Gly Leu Pro Asn
            355                 360                 365

Ser Leu Asp Ala Ala Leu Gln Tyr Thr Asn Gly Tyr Thr Tyr Phe Phe
        370                 375                 380

Lys Gly Asp Lys Tyr Tyr Arg Phe Asn Asp Arg Thr Phe Ala Val Ser
385                 390                 395                 400

Ile Ser Leu Ile

<210> SEQ ID NO 35
<211> LENGTH: 430
<212> TYPE: PRT
<213> ORGANISM: Malus domestica

<400> SEQUENCE: 35

Met Glu Leu Met Ser Leu Pro Arg Cys Gly Val Arg Asp Lys Val Gly
1               5                   10                  15

Phe Gly Asn Asp Asn Arg Ser Lys Arg Tyr Ala Leu Gln Gly Ser Arg
            20                  25                  30

Trp Arg Val Lys Ala Leu Thr Tyr Lys Ile Ser Lys Tyr Pro Lys Arg
        35                  40                  45

Leu Lys Lys Ala Asp Val Asp Ala Glu Ile Arg Ala Phe Ala Val
50                  55                  60

Trp Ser Glu Tyr Thr Asp Leu Ser Phe Thr Pro Lys Ser Gly Pro
65                  70                  75                  80

Val His Ile Glu Ile Lys Phe Val Glu Ser Glu His Gly Asp Gly Asp
                85                  90                  95

Ala Phe Asp Gly Val Gly Gly Thr Leu Ala His Ala Phe Phe Pro Val
                100                 105                 110

Phe Gly Gly Asp Ala His Phe Asp Asp Ala Glu Leu Trp Thr Ile Gly
            115                 120                 125

Ser Pro Arg Gly Thr Asn Leu Phe Gln Val Ala Ala His Glu Phe Gly
```

```
                    130                 135                 140
His Ser Leu Gly Leu Ser His Ser Asp Val Arg Ser Ala Leu Met Ala
145                 150                 155                 160

Pro Phe Tyr Arg Gly Phe Glu Pro Val Phe Lys Leu Asp Ser Asp Asp
                    165                 170                 175

Val Leu Ala Ile Gln Ala Leu Tyr Gly Lys Lys Ser Ser Asn Gly
                180                 185                 190

Asn Gly Ile Asn Pro Pro Ser Gly Gly Ala Phe Pro Arg Thr Thr Gln
                195                 200                 205

Arg Pro Ala Phe Ala Pro Pro Arg Thr Pro Arg Asp Asp Gln Leu Cys
210                 215                 220

Lys Asp Pro Lys Ile Asp Ala Leu Phe Asn Ser Ala Asp Gly Gln Thr
225                 230                 235                 240

Tyr Ala Leu Lys Gly Asn Lys Tyr Tyr Lys Leu Thr Glu Asn Ser Val
                245                 250                 255

Ala Asp Gly Tyr Pro Lys Leu Ile Ser Glu Gly Trp Pro Gly Leu Pro
                260                 265                 270

Gly Asp Ile Asp Ala Ala Phe Thr Tyr Lys Asn Gly Lys Thr Tyr Phe
                275                 280                 285

Phe Lys Gly Thr Lys Tyr Trp Arg Tyr Asn Gly Arg Gln Met Asp Gly
290                 295                 300

Asp Tyr Pro Lys Glu Ile Ser Glu Gly Phe Thr Gly Val Pro Asp His
305                 310                 315                 320

Leu Asp Ala Ala Met Val Trp Gly Gly Asn Gly Lys Ile Tyr Phe Tyr
                325                 330                 335

Lys Gly Ser Lys Phe Trp Arg Phe Asp Pro Leu Lys Arg Pro Pro Val
                340                 345                 350

Lys Ser Ser Tyr Pro Lys Pro Ile Ser Asn Trp Glu Gly Leu Pro Asn
                355                 360                 365

Ser Leu Asp Ala Ala Leu Gln Tyr Thr Asn Gly Tyr Thr Tyr Phe Phe
                370                 375                 380

Lys Gly Asp Lys Tyr Tyr Arg Phe Asn Asp Arg Thr Phe Ala Val Asp
385                 390                 395                 400

Ala Ala Asp Pro Pro Phe Pro Arg Pro Ser Ala His Trp Trp Phe Gly
                405                 410                 415

Cys Lys Asn Thr Pro Ser Thr Thr Gly Val Arg Lys Arg Gly
                420                 425                 430

<210> SEQ ID NO 36
<211> LENGTH: 514
<212> TYPE: PRT
<213> ORGANISM: Tribolium castaneum

<400> SEQUENCE: 36

Met Arg His Thr Val Ile Ser Phe Thr Leu Phe Ala Thr Leu Leu Gln
1               5                   10                  15

Leu Ser Lys Ser Ala Pro Ser Gly Ser Ser Ala Leu Leu Tyr Leu Ser
                20                  25                  30

Gln Tyr Gly Tyr Leu Gly Gly Asn Leu Arg Ser Leu Asn Ser Ser Ala
            35                  40                  45

Leu Thr Asp Glu Arg Val Leu Arg Lys Ala Val Glu Asp Phe Gln Ser
        50                  55                  60

Phe Ala Gly Leu Asp Val Thr Gly Glu Leu Asp Asp Arg Thr Leu Lys
65                  70                  75                  80
```

-continued

```
Glu Met Gln Leu Pro Arg Cys Gly Val Lys Asp Lys Val Gly Thr Gly
                 85                  90                  95
Asp Asn Arg Ala Lys Arg Tyr Ala Leu Gln Gly Ser Arg Trp Lys Val
            100                 105                 110
Lys Asn Leu Asn Tyr Lys Ile Ser Lys Tyr Pro Lys Asn Leu Asn Thr
        115                 120                 125
Lys Glu Val Asp Lys Glu Ile His Arg Ala Phe Ser Val Trp Ser Gln
    130                 135                 140
Tyr Thr Asp Leu Thr Phe Thr Pro Ser Lys Gly Ser Ala His Ile Glu
145                 150                 155                 160
Ile Arg Phe Glu Ser Gly Glu His Gly Asp Gly Asp Pro Phe Asp Gly
                165                 170                 175
Pro Gly Gly Thr Leu Ala His Ala Tyr Phe Pro Val Phe Gly Gly Asp
            180                 185                 190
Ala His Phe Asp Ala Ser Glu Lys Trp Thr Ile Asn Ser Tyr Arg Gly
        195                 200                 205
Thr Asn Leu Phe Gln Val Ala Ala His Glu Phe Gly His Ser Leu Gly
    210                 215                 220
Leu Ser His Ser Asp Val Arg Glu Ala Leu Met Ala Pro Phe Tyr Arg
225                 230                 235                 240
Gly Tyr Asp Pro Leu Phe Glu Leu His Glu Asp Ile Gln Gly Ile Gln
                245                 250                 255
Gln Ala Leu Tyr Gly Lys Lys Thr Arg Lys Pro Gly Gly Gly Gly Gly
            260                 265                 270
Gly Tyr Asp Asp Ser Asp Phe Gln Gly Ser Asn Pro Gly His Arg
        275                 280                 285
Val Pro Ala Pro Ala Pro Thr Pro Val Asp Ser Asn Leu Cys Lys Asn
290                 295                 300
Pro Lys Ile Asp Thr Ile Phe Asn Ser Ala Glu Gly Tyr Thr Tyr Ile
305                 310                 315                 320
Phe Lys Gly Asp Lys Tyr Trp Lys Leu Thr Glu Glu Ser Val Ala Pro
                325                 330                 335
Gly Tyr Pro Lys Ala Ile Ser Ser Gly Trp Pro Gly Leu Pro Gly Asp
            340                 345                 350
Ile Asp Ala Ala Phe Thr Tyr Lys Asn Gly Lys Thr Tyr Phe Phe Lys
        355                 360                 365
Gly Ser Lys Tyr Trp Arg Tyr Lys Gly Arg Lys Val Asp Gly Asp Tyr
    370                 375                 380
Pro Lys Glu Ile Ser Glu Gly Phe Thr Gly Ile Pro Asp Asp Leu Asp
385                 390                 395                 400
Ala Ala Met Val Trp Ser Gly Asn Gly Lys Ile Tyr Phe Phe Lys Gly
                405                 410                 415
Ala Lys Phe Trp Arg Phe Asp Pro Ser Gln Arg Pro Val Lys Ser
            420                 425                 430
Thr Tyr Pro Lys Pro Ile Ser Asn Trp Glu Gly Val Pro Asn Asn Leu
        435                 440                 445
Asp Ala Ala Phe Lys Trp Thr Asn Gly Tyr Thr Tyr Phe Tyr Lys Gly
    450                 455                 460
Asp Ala Tyr Tyr Arg Phe Asn Asp Arg Ala Phe Ala Val Asp Lys Ala
465                 470                 475                 480
Ser Pro Ala Phe Pro Arg Ala Ile Ala Tyr Trp Trp Leu Gly Cys Ser
                485                 490                 495
Asn Ala Pro Gln Gly Thr Ile Gly Thr Lys Asn Tyr Arg Arg Pro Ala
```

Ser His

<210> SEQ ID NO 37
<211> LENGTH: 536
<212> TYPE: PRT
<213> ORGANISM: Culex quinuefasciatus

<400> SEQUENCE: 37

Met Glu Val Phe Ala Thr Val Leu Val Leu Leu Ala Ala Val Thr Cys
1               5                   10                  15

Ile Gly Asp Gly Phe Pro Leu Tyr Leu Ser Gln Phe Gly Tyr Leu Ser
            20                  25                  30

Ala Lys Phe Arg Asn Pro Thr Ser Gly Asn Leu Leu Asp Lys Asp Ser
        35                  40                  45

Trp Glu Lys Ala Ile Met Asp Phe Gln Ser Phe Ala Gly Leu Asn Val
    50                  55                  60

Ser Gly Glu Leu Asp Pro Glu Thr Met Glu Leu Met Ser Leu Pro Arg
65                  70                  75                  80

Cys Gly Val Arg Asp Lys Val Gly Phe Gly Thr Asp Ser Arg Ser Lys
                85                  90                  95

Arg Tyr Ala Leu Gln Gly Ser Arg Trp Lys Val Lys Ala Leu Thr Tyr
            100                 105                 110

Arg Ile Ser Lys Tyr Pro Ala Arg Leu Asp Arg Leu Glu Val Glu Lys
        115                 120                 125

Glu Ile Ala Lys Ala Phe Ser Val Trp Ser Gly Tyr Thr Asp Leu Thr
130                 135                 140

Phe Thr Pro Lys Lys Ser Ala Pro Val His Ile Asp Ile Arg Phe Glu
145                 150                 155                 160

Val Asn Glu His Gly Asp Gly Asp Pro Phe Asp Gly Pro Gly Gly Thr
                165                 170                 175

Leu Ala His Ala Tyr Phe Pro Val Tyr Gly Gly Asp Ala His Phe Asp
            180                 185                 190

Asp Ala Glu Phe Trp Thr Ile Gly Lys Ser Arg Gly Thr Asn Leu Phe
        195                 200                 205

Gln Val Ala Ala His Glu Phe Gly His Ser Leu Gly Leu Ser His Ser
210                 215                 220

Asp Val Arg Ser Ala Leu Met Ala Pro Phe Tyr Arg Gly Tyr Asp Pro
225                 230                 235                 240

Val Phe Arg Leu Asp Ser Asp Val Gln Gly Ile Gln Ala Leu Tyr
                245                 250                 255

Gly Arg Lys Thr Asn Gly Gly Ser Asn Gly Gly Ser Gly Ser Ser
            260                 265                 270

Pro Thr Arg Pro Thr Gln Arg Pro Val Gln Lys Asp Pro Asp Ser Glu
        275                 280                 285

Leu Cys Ser Ser Pro Lys Ile Asp Ala Ile Phe Asn Ser Ala Asp Gly
290                 295                 300

Ala Thr Tyr Ala Phe Lys Gly Asp Ser Tyr Tyr Lys Leu Thr Glu Asn
305                 310                 315                 320

Ala Val Ala Glu Gly Tyr Pro Lys Lys Ile Ala Glu Gly Trp Pro Gln
                325                 330                 335

Leu Pro Gly Asn Ile Asp Ala Ala Phe Thr Tyr Lys Asn Gly Lys Thr
            340                 345                 350

Tyr Phe Phe Gln Gly Thr Lys Tyr Trp Arg Tyr Ser Gly Arg Gln Met

```
            355                 360                 365
Asp Gly Asp Tyr Pro Lys Glu Ile Ser Glu Gly Phe Thr Gly Val Pro
            370                 375                 380
Asp His Leu Asp Ala Ala Leu Val Trp Gly Gly Asn Gly Lys Ile Tyr
385                 390                 395                 400
Phe Tyr Lys Gly Ser Lys Phe Trp Arg Phe Asp Pro Leu Lys Arg Pro
                405                 410                 415
Pro Val Lys Ser Thr Tyr Pro Lys Pro Ile Ser Asn Trp Glu Gly Leu
            420                 425                 430
Pro Asn Asn Ile Asp Ala Ala Leu Gln Tyr Thr Asn Gly Tyr Thr Tyr
        435                 440                 445
Phe Phe Lys Asp Asp Lys Tyr Tyr Arg Phe Asn Asp Arg Thr Phe Ser
450                 455                 460
Ile Asp Gln Ser Asp Pro Pro Phe Pro Arg Pro Val Ala His Trp Trp
465                 470                 475                 480
Tyr Gly Cys Lys Asn Ser Pro Ser Thr Phe Asp Ser Ile Ala Gly Pro
                485                 490                 495
Asp Thr Asn Asp Arg Pro Ala Gly Asp Tyr Asn Ser Gly Ser Gly
            500                 505                 510
Ala Ser Phe Ile Arg Leu Asn Val Ser Ile Ile Leu Ala Val Ala Val
        515                 520                 525
Leu Leu Gly Phe Ala Arg Lys Leu
            530                 535

<210> SEQ ID NO 38
<211> LENGTH: 577
<212> TYPE: PRT
<213> ORGANISM: Bombyx mori

<400> SEQUENCE: 38

Met Arg Ile Ile Lys Asn Thr Lys Gly Ile Ser Arg Gly Ile Met Ala
1               5                   10                  15
Met Met Thr Met Arg Gly Gly Leu Arg Ile Leu Trp Thr Val Ala Ala
            20                  25                  30
Ala Gly Val Leu Leu Thr Arg Ser Ser Ala Ala Pro Thr Phe Gly Thr
        35                  40                  45
Thr Asp Lys Ala Thr Met Tyr Leu Ala Gln Tyr Gly Tyr Leu Ser Pro
    50                  55                  60
Ser Val Arg Asn Pro Ser Ser Gly His Ile Met Asp Glu Ser Ser Trp
65                  70                  75                  80
Arg Arg Ala Ile Ala Glu Phe Gln Ser Phe Ala Gly Leu Asn Ala Thr
                85                  90                  95
Gly Glu Leu Asp Asp Gln Thr Asn Glu Met Met Ser Leu Pro Arg Cys
            100                 105                 110
Gly Val Arg Asp Lys Val Gly Phe Gly Glu Ser Arg Ala Lys Arg Tyr
        115                 120                 125
Ala Leu Gln Gly Ser Arg Trp Arg Val Lys Asn Leu Thr Tyr Lys Ile
    130                 135                 140
Ser Lys Tyr Pro Ser Arg Leu Asn Arg Ala Glu Val Asp Ala Glu Leu
145                 150                 155                 160
Ala Lys Ala Phe Ser Val Trp Ser Asp Tyr Thr Asp Leu Thr Phe Thr
                165                 170                 175
Gln Lys Arg Ser Gly Gln Val His Ile Glu Ile Arg Phe Glu Lys Gly
            180                 185                 190
```

```
Glu His Gly Asp Gly Asp Pro Phe Asp Gly Pro Gly Thr Leu Ala
            195                 200                 205

His Ala Tyr Phe Pro Ala His Gln Ile Ala Met Gln Tyr Val Lys Arg
210                 215                 220

Asp Leu Gln Ser Asp Val Tyr Thr Val Tyr Gly Gly Asp Ala His Phe
225                 230                 235                 240

Asp Asp Ala Glu Met Trp Ser Ile Asn Ser Arg Gly Thr Asn Leu
            245                 250                 255

Phe Gln Val Ala Ala His Glu Phe Gly His Ser Leu Gly Leu Ser His
                260                 265                 270

Ser Asp Val Arg Ser Ala Leu Met Ala Pro Tyr Arg Gly Tyr Asp
            275                 280                 285

Pro Ala Phe Gln Leu Asp Gln Asp Val Gln Gly Ile Gln Ser Leu
290                 295                 300

Tyr Gly His Lys Thr Gln Thr Asp Ile Gly Gly Gly Gly Gly Leu
305                 310                 315                 320

Ile Pro Ser Val Pro Arg Ala Thr Thr Gln Gln Pro Ser Ala Glu Asp
                325                 330                 335

Pro Ala Leu Cys Ala Asp Pro Arg Ile Asp Thr Ile Phe Asn Ser Ala
            340                 345                 350

Asp Gly Ser Thr Phe Val Phe Lys Gly Asp His Tyr Trp Arg Leu Thr
            355                 360                 365

Glu Asp Gly Val Ala Ala Gly Tyr Pro Arg Leu Ile Ser Arg Ala Trp
370                 375                 380

Pro Gly Leu Pro Gly Asn Ile Asp Ala Ala Phe Thr Tyr Lys Asn Gly
385                 390                 395                 400

Lys Thr Tyr Phe Phe Lys Gly Ser Lys Tyr Trp Arg Tyr Asn Gly Gln
                405                 410                 415

Lys Met Asp Gly Asp Tyr Pro Lys Asp Ile Ser Glu Gly Phe Thr Gly
            420                 425                 430

Ile Pro Asp Asn Leu Asp Ala Ala Leu Val Trp Ser Gly Asn Gly Lys
            435                 440                 445

Ile Tyr Phe Tyr Lys Gly Ser Lys Phe Trp Arg Phe Asp Pro Ala Gln
450                 455                 460

Arg Pro Pro Val Lys Ala Thr Tyr Pro Lys Pro Leu Ser Asn Trp Asp
465                 470                 475                 480

Gly Ile Pro Asp Asn Ile Asp Ala Ala Leu Gln Tyr Thr Asn Gly Tyr
                485                 490                 495

Thr Tyr Phe Phe Lys Gly Gly Ser Tyr Trp Arg Phe Asn Asp Arg Leu
            500                 505                 510

Phe Ser Val Asp Thr Asp Asn Pro Gln Phe Pro Arg Ser Thr Ala Phe
            515                 520                 525

Trp Trp Leu Gly Cys Ser Ser Ala Pro Arg Gly Thr Val Gly Asp Asp
530                 535                 540

Gly Thr Pro Ser Leu Glu Asn Asp Gly Val Ile Ala Arg Pro Thr Leu
545                 550                 555                 560

Thr Ser Val Leu Val Val Val Thr Thr Leu Arg His Val Leu Arg
                565                 570                 575

Thr
```

<210> SEQ ID NO 39
<211> LENGTH: 512
<212> TYPE: PRT
<213> ORGANISM: Drosophila melanogaster

<400> SEQUENCE: 39

```
Met Thr Asn Cys Gln Ser Ser Val Phe Ile Val Val Gly Thr Leu Phe
1               5                   10                  15

Ser Ile Met Ala Ala Ala Gln Ser Ala Pro Val Ser Thr Thr Thr Gln
            20                  25                  30

Ala Glu Ile Tyr Leu Ser Gln Phe Gly Tyr Leu Pro Ala Ser Ala Arg
                35                  40                  45

Asn Pro Ala Ser Ser Gly Leu His Asp Gln Arg Thr Trp Val Ser Ala
        50                  55                  60

Ile Glu Glu Phe Gln Ser Phe Ala Gly Leu Asn Ile Thr Gly Glu Leu
65                  70                  75                  80

Asp Ala Glu Thr Met Lys Leu Met Ser Leu Pro Arg Cys Gly Val Arg
                85                  90                  95

Asp Arg Val Gly Thr Gly Asp Ser Arg Ser Lys Arg Tyr Ala Leu Gln
            100                 105                 110

Gly Ser Arg Trp Arg Val Lys Asn Leu Thr Tyr Lys Ile Ser Lys Tyr
        115                 120                 125

Pro Lys Arg Leu Lys Arg Val Asp Val Asp Ala Glu Ile Gly Arg Ala
    130                 135                 140

Phe Ala Val Trp Ser Glu Asp Thr Asp Leu Thr Phe Thr Arg Lys Thr
145                 150                 155                 160

Ser Gly Pro Val His Ile Glu Ile Lys Phe Val Glu Ser Glu His Gly
                165                 170                 175

Asp Gly Asp Ala Phe Asp Gly Gln Gly Gly Thr Leu Ala His Ala Phe
            180                 185                 190

Phe Pro Val Phe Gly Gly Asp Ala His Phe Asp Asp Ala Glu Leu Trp
        195                 200                 205

Thr Ile Gly Ser Pro Arg Gly Thr Asn Leu Phe Gln Val Ala Ala His
    210                 215                 220

Glu Phe Gly His Ser Leu Gly Leu Ser His Ser Asp Gln Ser Ser Ala
225                 230                 235                 240

Leu Met Ala Pro Phe Tyr Arg Gly Phe Glu Pro Val Phe Lys Leu Asp
                245                 250                 255

Glu Asp Asp Lys Ala Ala Ile Gln Ser Leu Tyr Gly Arg Lys Thr Asn
            260                 265                 270

Gln Leu Arg Pro Thr Asn Val Tyr Pro Ala Thr Thr Gln Arg Pro Tyr
        275                 280                 285

Ser Pro Pro Lys Val Pro Leu Asp Asp Ser Ile Cys Lys Asp Ser Lys
    290                 295                 300

Val Asp Thr Leu Phe Asn Ser Ala Gln Gly Glu Thr Tyr Ala Phe Lys
305                 310                 315                 320

Gly Asp Lys Tyr Tyr Lys Leu Thr Thr Asp Ser Val Glu Glu Gly Tyr
                325                 330                 335

Pro Gln Leu Ile Ser Lys Gly Trp Pro Gly Leu Pro Gly Asn Ile Asp
            340                 345                 350

Ala Ala Phe Thr Tyr Lys Asn Gly Lys Thr Tyr Phe Phe Lys Gly Thr
        355                 360                 365

Gln Tyr Trp Arg Tyr Gln Gly Arg Gln Met Asp Gly Val Tyr Pro Lys
    370                 375                 380

Glu Ile Ser Glu Gly Phe Thr Gly Ile Pro Asp His Leu Asp Ala Ala
385                 390                 395                 400

Met Val Trp Gly Gly Asn Gly Lys Ile Tyr Phe Phe Lys Gly Ser Lys
```

```
              405                 410                 415
Phe Trp Arg Phe Asp Pro Ala Lys Arg Pro Val Lys Ala Ser Tyr
            420                 425                 430

Pro Lys Pro Ile Ser Asn Trp Glu Gly Val Pro Asn Asn Leu Asp Ala
            435                 440                 445

Ala Leu Lys Tyr Thr Asn Gly Tyr Thr Tyr Phe Phe Lys Gly Asp Lys
            450                 455                 460

Tyr Tyr Arg Phe His Asp Ala Arg Phe Ala Val Asp Ser Ala Thr Pro
465             470                 475                 480

Pro Phe Pro Arg Pro Thr Ala His Trp Trp Phe Gly Cys Lys Asn Thr
            485                 490                 495

Pro Ser Ser Thr Gly Phe Lys Arg Arg Gly Tyr Lys Asn Lys Asn Asn
            500                 505                 510

<210> SEQ ID NO 40
<211> LENGTH: 469
<212> TYPE: PRT
<213> ORGANISM: Homo sapiens

<400> SEQUENCE: 40

Met His Ser Phe Pro Pro Leu Leu Leu Leu Phe Trp Gly Val Val
1               5                   10                  15

Ser His Ser Phe Pro Ala Thr Leu Glu Thr Gln Glu Gln Asp Val Asp
                20                  25                  30

Leu Val Gln Lys Tyr Leu Glu Lys Tyr Tyr Asn Leu Lys Asn Asp Gly
            35                  40                  45

Arg Gln Val Glu Lys Arg Arg Asn Ser Gly Pro Val Val Glu Lys Leu
50                  55                  60

Lys Gln Met Gln Glu Phe Phe Gly Leu Lys Val Thr Gly Lys Pro Asp
65                  70                  75                  80

Ala Glu Thr Leu Lys Val Met Lys Gln Pro Arg Cys Gly Val Pro Asp
                85                  90                  95

Val Ala Gln Phe Val Leu Thr Glu Gly Asn Pro Arg Trp Glu Gln Thr
            100                 105                 110

His Leu Thr Tyr Arg Ile Glu Asn Tyr Thr Pro Asp Leu Pro Arg Ala
        115                 120                 125

Asp Val Asp His Ala Ile Glu Lys Ala Phe Gln Leu Trp Ser Asn Val
    130                 135                 140

Thr Pro Leu Thr Phe Thr Lys Val Ser Glu Gly Gln Ala Asp Ile Met
145                 150                 155                 160

Ile Ser Phe Val Arg Gly Asp His Arg Asp Asn Ser Pro Phe Asp Gly
                165                 170                 175

Pro Gly Gly Asn Leu Ala His Ala Phe Gln Pro Gly Pro Gly Ile Gly
            180                 185                 190

Gly Asp Ala His Phe Asp Glu Asp Glu Arg Trp Thr Asn Asn Phe Arg
        195                 200                 205

Glu Tyr Asn Leu His Arg Val Ala Ala His Glu Leu Gly His Ser Leu
    210                 215                 220

Gly Leu Ser His Ser Thr Asp Ile Gly Ala Leu Met Tyr Pro Ser Tyr
225                 230                 235                 240

Thr Phe Ser Gly Asp Val Gln Leu Ala Gln Asp Asp Ile Asp Gly Ile
                245                 250                 255

Gln Ala Ile Tyr Gly Arg Ser Gln Asn Pro Val Gln Pro Ile Gly Pro
            260                 265                 270
```

```
Gln Thr Pro Lys Ala Cys Asp Ser Lys Leu Thr Phe Asp Ala Ile Thr
            275                 280                 285

Thr Ile Arg Gly Glu Val Met Phe Phe Lys Asp Arg Phe Tyr Met Arg
290                 295                 300

Thr Asn Pro Phe Tyr Pro Glu Val Glu Leu Asn Phe Ile Ser Val Phe
305                 310                 315                 320

Trp Pro Gln Leu Pro Asn Gly Leu Glu Ala Ala Tyr Glu Phe Ala Asp
                325                 330                 335

Arg Asp Glu Val Arg Phe Phe Lys Gly Asn Lys Tyr Trp Ala Val Gln
            340                 345                 350

Gly Gln Asn Val Leu His Gly Tyr Pro Lys Asp Ile Tyr Ser Ser Phe
        355                 360                 365

Gly Phe Pro Arg Thr Val Lys His Ile Asp Ala Ala Leu Ser Glu Glu
370                 375                 380

Asn Thr Gly Lys Thr Tyr Phe Phe Val Ala Asn Lys Tyr Trp Arg Tyr
385                 390                 395                 400

Asp Glu Tyr Lys Arg Ser Met Asp Pro Gly Tyr Pro Lys Met Ile Ala
                405                 410                 415

His Asp Phe Pro Gly Ile Gly His Lys Val Asp Ala Val Phe Met Lys
            420                 425                 430

Asp Gly Phe Phe Tyr Phe Phe His Gly Thr Arg Gln Tyr Lys Phe Asp
        435                 440                 445

Pro Lys Thr Lys Arg Ile Leu Thr Leu Gln Lys Ala Asn Ser Trp Phe
    450                 455                 460

Asn Cys Arg Lys Asn
465

<210> SEQ ID NO 41
<211> LENGTH: 467
<212> TYPE: PRT
<213> ORGANISM: Homo sapiens

<400> SEQUENCE: 41

Met Phe Ser Leu Lys Thr Leu Pro Phe Leu Leu Leu Leu His Val Gln
1               5                   10                  15

Ile Ser Lys Ala Phe Pro Val Ser Ser Lys Glu Lys Asn Thr Lys Ile
            20                  25                  30

Val Gln Asp Tyr Leu Glu Lys Phe Tyr Gln Leu Pro Ser Asn Gln Tyr
        35                  40                  45

Gln Ser Thr Arg Lys Asn Gly Thr Asn Val Ile Val Glu Lys Leu Lys
    50                  55                  60

Glu Met Gln Arg Phe Phe Gly Leu Asn Val Thr Gly Lys Pro Asn Glu
65                  70                  75                  80

Glu Thr Leu Asp Met Met Lys Lys Pro Arg Cys Gly Val Pro Asp Ser
                85                  90                  95

Gly Gly Phe Met Leu Thr Pro Gly Asn Pro Lys Trp Glu Arg Thr Asn
            100                 105                 110

Leu Thr Tyr Arg Ile Arg Asn Tyr Thr Pro Gln Leu Ser Glu Ala Glu
        115                 120                 125

Val Glu Arg Ala Ile Lys Asp Ala Phe Glu Leu Trp Ser Val Ala Ser
    130                 135                 140

Pro Leu Ile Phe Thr Arg Ile Ser Gln Gly Glu Ala Asp Ile Asn Ile
145                 150                 155                 160

Ala Phe Tyr Gln Arg Asp His Gly Asp Asn Ser Pro Phe Asp Gly Pro
                165                 170                 175
```

```
Asn Gly Ile Leu Ala His Ala Phe Gln Pro Gly Gln Gly Ile Gly Gly
                180                 185                 190

Asp Ala His Phe Asp Ala Glu Glu Thr Trp Thr Asn Thr Ser Ala Asn
            195                 200                 205

Tyr Asn Leu Phe Leu Val Ala Ala His Glu Phe Gly His Ser Leu Gly
    210                 215                 220

Leu Ala His Ser Ser Asp Pro Gly Ala Leu Met Tyr Pro Asn Tyr Ala
225                 230                 235                 240

Phe Arg Glu Thr Ser Asn Tyr Ser Leu Pro Gln Asp Ile Asp Gly
                245                 250                 255

Ile Gln Ala Ile Tyr Gly Leu Ser Asn Pro Ile Gln Pro Thr Gly
            260                 265                 270

Pro Ser Thr Pro Lys Pro Cys Asp Pro Ser Leu Thr Phe Asp Ala Ile
        275                 280                 285

Thr Thr Leu Arg Gly Glu Ile Leu Phe Phe Lys Asp Arg Tyr Phe Trp
    290                 295                 300

Arg Arg His Pro Gln Leu Gln Arg Val Glu Met Asn Phe Ile Ser Leu
305                 310                 315                 320

Phe Trp Pro Ser Leu Pro Thr Gly Ile Gln Ala Ala Tyr Glu Asp Phe
                325                 330                 335

Asp Arg Asp Leu Ile Phe Leu Phe Lys Gly Asn Gln Tyr Trp Ala Leu
            340                 345                 350

Ser Gly Tyr Asp Ile Leu Gln Gly Tyr Pro Lys Asp Ile Ser Asn Tyr
        355                 360                 365

Gly Phe Pro Ser Ser Val Gln Ala Ile Asp Ala Ala Val Phe Tyr Arg
    370                 375                 380

Ser Lys Thr Tyr Phe Phe Val Asn Asp Gln Phe Trp Arg Tyr Asp Asn
385                 390                 395                 400

Gln Arg Gln Phe Met Glu Pro Gly Tyr Pro Lys Ser Ile Ser Gly Ala
                405                 410                 415

Phe Pro Gly Ile Glu Ser Lys Val Asp Ala Val Phe Gln Gln Glu His
            420                 425                 430

Phe Phe His Val Phe Ser Gly Pro Arg Tyr Tyr Ala Phe Asp Leu Ile
        435                 440                 445

Ala Gln Arg Val Thr Arg Val Ala Arg Gly Asn Lys Trp Leu Asn Cys
    450                 455                 460

Arg Tyr Gly
465

<210> SEQ ID NO 42
<211> LENGTH: 471
<212> TYPE: PRT
<213> ORGANISM: Homo sapiens

<400> SEQUENCE: 42

Met His Pro Gly Val Leu Ala Ala Phe Leu Phe Leu Ser Trp Thr His
1               5                   10                  15

Cys Arg Ala Leu Pro Leu Pro Ser Gly Gly Asp Glu Asp Asp Leu Ser
            20                  25                  30

Glu Glu Asp Leu Gln Phe Ala Glu Arg Tyr Leu Arg Ser Tyr Tyr His
        35                  40                  45

Pro Thr Asn Leu Ala Gly Ile Leu Lys Glu Asn Ala Ala Ser Ser Met
    50                  55                  60

Thr Glu Arg Leu Arg Glu Met Gln Ser Phe Phe Gly Leu Glu Val Thr
```

```
            65                  70                  75                  80
        Gly Lys Leu Asp Asp Asn Thr Leu Asp Val Met Lys Lys Pro Arg Cys
                         85                  90                  95
        Gly Val Pro Asp Val Gly Glu Tyr Asn Val Phe Pro Arg Thr Leu Lys
                        100                 105                 110
        Trp Ser Lys Met Asn Leu Thr Tyr Arg Ile Val Asn Tyr Thr Pro Asp
                        115                 120                 125
        Met Thr His Ser Glu Val Glu Lys Ala Phe Lys Lys Ala Phe Lys Val
                        130                 135                 140
        Trp Ser Asp Val Thr Pro Leu Asn Phe Thr Arg Leu His Asp Gly Ile
        145                 150                 155                 160
        Ala Asp Ile Met Ile Ser Phe Gly Ile Lys Glu His Gly Asp Phe Tyr
                        165                 170                 175
        Pro Phe Asp Gly Pro Ser Gly Leu Leu Ala His Ala Phe Pro Pro Gly
                        180                 185                 190
        Pro Asn Tyr Gly Gly Asp Ala His Phe Asp Asp Asp Glu Thr Trp Thr
                        195                 200                 205
        Ser Ser Ser Lys Gly Tyr Asn Leu Phe Leu Val Ala Ala His Glu Phe
                        210                 215                 220
        Gly His Ser Leu Gly Leu Asp His Ser Lys Asp Pro Gly Ala Leu Met
        225                 230                 235                 240
        Phe Pro Ile Tyr Thr Tyr Thr Gly Lys Ser His Phe Met Leu Pro Asp
                        245                 250                 255
        Asp Asp Val Gln Gly Ile Gln Ser Leu Tyr Gly Pro Gly Asp Glu Asp
                        260                 265                 270
        Pro Asn Pro Lys His Pro Lys Thr Pro Asp Lys Cys Asp Pro Ser Leu
                        275                 280                 285
        Ser Leu Asp Ala Ile Thr Ser Leu Arg Gly Glu Thr Met Ile Phe Lys
                        290                 295                 300
        Asp Arg Phe Phe Trp Arg Leu His Pro Gln Gln Val Asp Ala Glu Leu
        305                 310                 315                 320
        Phe Leu Thr Lys Ser Phe Trp Pro Glu Leu Pro Asn Arg Ile Asp Ala
                        325                 330                 335
        Ala Tyr Glu His Pro Ser His Asp Leu Ile Phe Ile Phe Arg Gly Arg
                        340                 345                 350
        Lys Phe Trp Ala Leu Asn Gly Tyr Asp Ile Leu Glu Gly Tyr Pro Lys
                        355                 360                 365
        Lys Ile Ser Glu Leu Gly Leu Pro Lys Glu Val Lys Lys Ile Ser Ala
                        370                 375                 380
        Ala Val His Phe Glu Asp Thr Gly Lys Thr Leu Leu Phe Ser Gly Asn
        385                 390                 395                 400
        Gln Val Trp Arg Tyr Asp Asp Thr Asn His Ile Met Asp Lys Asp Tyr
                        405                 410                 415
        Pro Arg Leu Ile Glu Glu Asp Phe Pro Gly Ile Gly Asp Lys Val Asp
                        420                 425                 430
        Ala Val Tyr Glu Lys Asn Gly Tyr Ile Tyr Phe Phe Asn Gly Pro Ile
                        435                 440                 445
        Gln Phe Glu Tyr Ser Ile Trp Ser Asn Arg Ile Val Arg Val Met Pro
                        450                 455                 460
        Ala Asn Ser Ile Leu Trp Cys
        465                 470

<210> SEQ ID NO 43
```

```
<211> LENGTH: 584
<212> TYPE: PRT
<213> ORGANISM: Homo sapiens

<400> SEQUENCE: 43

Met Gln Lys Phe Phe Gly Leu Pro Gln Thr Gly Asp Leu Asp Gln Asn
1               5                   10                  15

Thr Ile Glu Thr Met Arg Lys Pro Arg Cys Gly Asn Pro Asp Val Ala
            20                  25                  30

Asn Tyr Asn Phe Phe Pro Arg Lys Pro Lys Trp Asp Lys Asn Gln Ile
        35                  40                  45

Thr Tyr Arg Ile Ile Gly Tyr Thr Pro Asp Leu Asp Pro Glu Thr Val
    50                  55                  60

Asp Asp Ala Phe Ala Arg Ala Phe Gln Val Trp Ser Asp Val Thr Pro
65                  70                  75                  80

Leu Arg Phe Ser Arg Ile His Asp Gly Glu Ala Asp Ile Met Ile Asn
                85                  90                  95

Phe Gly Arg Trp Glu His Gly Asp Gly Tyr Pro Phe Asp Gly Lys Asp
            100                 105                 110

Gly Leu Leu Ala His Ala Phe Ala Pro Gly Thr Gly Val Gly Gly Asp
        115                 120                 125

Ser His Phe Asp Asp Asp Glu Leu Trp Thr Leu Gly Glu Gly Gln Val
    130                 135                 140

Val Arg Val Lys Tyr Gly Asn Ala Asp Gly Glu Tyr Cys Lys Phe Pro
145                 150                 155                 160

Phe Leu Phe Asn Gly Lys Glu Tyr Asn Ser Cys Thr Asp Thr Gly Arg
                165                 170                 175

Ser Asp Gly Phe Leu Trp Cys Ser Thr Thr Tyr Asn Phe Glu Lys Asp
            180                 185                 190

Gly Lys Tyr Gly Phe Cys Pro His Glu Ala Leu Phe Thr Met Gly Gly
        195                 200                 205

Asn Ala Glu Gly Gln Pro Cys Lys Phe Pro Phe Arg Phe Gln Gly Thr
    210                 215                 220

Ser Tyr Asp Ser Cys Thr Thr Glu Gly Arg Thr Asp Gly Tyr Arg Trp
225                 230                 235                 240

Cys Gly Thr Thr Glu Asp Tyr Asp Arg Asp Lys Lys Tyr Gly Phe Cys
                245                 250                 255

Pro Glu Thr Ala Met Ser Thr Val Gly Gly Asn Ser Glu Gly Ala Pro
            260                 265                 270

Cys Val Phe Pro Phe Thr Phe Leu Gly Asn Lys Tyr Glu Ser Cys Thr
        275                 280                 285

Ser Ala Gly Arg Ser Asp Gly Lys Met Trp Cys Ala Thr Thr Ala Asn
    290                 295                 300

Tyr Asp Asp Asp Arg Lys Trp Gly Phe Cys Pro Asp Gln Gly Tyr Ser
305                 310                 315                 320

Leu Phe Leu Val Ala Ala His Glu Phe Gly His Ala Met Gly Leu Glu
                325                 330                 335

His Ser Gln Asp Pro Gly Ala Leu Met Ala Pro Ile Tyr Thr Tyr Thr
            340                 345                 350

Lys Asn Phe Arg Leu Ser Gln Asp Asp Ile Lys Gly Ile Gln Glu Leu
        355                 360                 365

Tyr Gly Ala Ser Pro Asp Ile Asp Leu Gly Thr Gly Pro Thr Pro Thr
    370                 375                 380

Leu Gly Pro Val Thr Pro Glu Ile Cys Lys Gln Asp Ile Val Phe Asp
```

```
                385                 390                 395                 400
        Gly Ile Ala Gln Ile Arg Gly Glu Ile Phe Phe Phe Lys Asp Arg Phe
                        405                 410                 415

Ile Trp Arg Thr Val Thr Pro Arg Asp Lys Pro Met Gly Pro Leu Leu
                        420                 425                 430

Val Ala Thr Phe Trp Pro Glu Leu Pro Glu Lys Ile Asp Ala Val Tyr
                        435                 440                 445

Glu Ala Pro Gln Glu Glu Lys Ala Val Phe Phe Ala Gly Asn Glu Tyr
                    450                 455                 460

Trp Ile Tyr Ser Ala Ser Thr Leu Glu Arg Gly Tyr Pro Lys Pro Leu
        465                 470                 475                 480

Thr Ser Leu Gly Leu Pro Pro Asp Val Gln Arg Val Asp Ala Ala Phe
                        485                 490                 495

Asn Trp Ser Lys Asn Lys Lys Thr Tyr Ile Phe Ala Gly Asp Lys Phe
                        500                 505                 510

Trp Arg Tyr Asn Glu Val Lys Lys Lys Met Asp Pro Gly Phe Pro Lys
                        515                 520                 525

Leu Ile Ala Asp Ala Trp Asn Ala Ile Pro Asp Asn Leu Asp Ala Val
                    530                 535                 540

Val Asp Leu Gln Gly Gly Gly His Ser Tyr Phe Phe Lys Gly Ala Tyr
        545                 550                 555                 560

Tyr Leu Lys Leu Glu Asn Gln Ser Leu Lys Ser Val Lys Phe Gly Ser
                        565                 570                 575

Ile Lys Ser Asp Trp Leu Gly Cys
                        580

<210> SEQ ID NO 44
<211> LENGTH: 707
<212> TYPE: PRT
<213> ORGANISM: Homo sapiens

<400> SEQUENCE: 44

Met Ser Leu Trp Gln Pro Leu Val Leu Val Leu Leu Val Leu Gly Cys
1               5                   10                  15

Cys Phe Ala Ala Pro Arg Gln Arg Gln Ser Thr Leu Val Leu Phe Pro
                20                  25                  30

Gly Asp Leu Arg Thr Asn Leu Thr Asp Arg Gln Leu Ala Glu Glu Tyr
            35                  40                  45

Leu Tyr Arg Tyr Gly Tyr Thr Arg Val Ala Glu Met Arg Gly Glu Ser
    50                  55                  60

Lys Ser Leu Gly Pro Ala Leu Leu Leu Leu Gln Lys Gln Leu Ser Leu
65                  70                  75                  80

Pro Glu Thr Gly Glu Leu Asp Ser Ala Thr Leu Lys Ala Met Arg Thr
                85                  90                  95

Pro Arg Cys Gly Val Pro Asp Leu Gly Arg Phe Gln Thr Phe Glu Gly
                100                 105                 110

Asp Leu Lys Trp His His His Asn Ile Thr Tyr Trp Ile Gln Asn Tyr
            115                 120                 125

Ser Glu Asp Leu Pro Arg Ala Val Ile Asp Asp Ala Phe Ala Arg Ala
    130                 135                 140

Phe Ala Leu Trp Ser Ala Val Thr Pro Leu Thr Phe Thr Arg Val Tyr
145                 150                 155                 160

Ser Arg Asp Ala Asp Ile Val Ile Gln Phe Gly Val Ala Glu His Gly
                165                 170                 175
```

-continued

```
Asp Gly Tyr Pro Phe Asp Gly Lys Asp Gly Leu Leu Ala His Ala Phe
            180                 185                 190
Pro Pro Gly Pro Gly Ile Gln Gly Asp Ala His Phe Asp Asp Glu
        195                 200                 205
Leu Trp Ser Leu Gly Lys Gly Val Val Val Pro Thr Arg Phe Gly Asn
    210                 215                 220
Ala Asp Gly Ala Ala Cys His Phe Pro Phe Ile Phe Glu Gly Arg Ser
225                 230                 235                 240
Tyr Ser Ala Cys Thr Thr Asp Gly Arg Ser Asp Gly Leu Pro Trp Cys
                245                 250                 255
Ser Thr Thr Ala Asn Tyr Asp Thr Asp Asp Arg Phe Gly Phe Cys Pro
                260                 265                 270
Ser Glu Arg Leu Tyr Thr Gln Asp Gly Asn Ala Asp Gly Lys Pro Cys
                275                 280                 285
Gln Phe Pro Phe Ile Phe Gln Gly Gln Ser Tyr Ser Ala Cys Thr Thr
            290                 295                 300
Asp Gly Arg Ser Asp Gly Tyr Arg Trp Cys Ala Thr Thr Ala Asn Tyr
305                 310                 315                 320
Asp Arg Asp Lys Leu Phe Gly Phe Cys Pro Thr Arg Ala Asp Ser Thr
                325                 330                 335
Val Met Gly Gly Asn Ser Ala Gly Glu Leu Cys Val Phe Pro Phe Thr
                340                 345                 350
Phe Leu Gly Lys Glu Tyr Ser Thr Cys Thr Ser Glu Gly Arg Gly Asp
            355                 360                 365
Gly Arg Leu Trp Cys Ala Thr Thr Ser Asn Phe Asp Ser Asp Lys Lys
370                 375                 380
Trp Gly Phe Cys Pro Asp Gln Gly Tyr Ser Leu Phe Leu Val Ala Ala
385                 390                 395                 400
His Glu Phe Gly His Ala Leu Gly Leu Asp His Ser Ser Val Pro Glu
                405                 410                 415
Ala Leu Met Tyr Pro Met Tyr Arg Phe Thr Glu Gly Pro Pro Leu His
            420                 425                 430
Lys Asp Asp Val Asn Gly Ile Arg His Leu Tyr Gly Pro Arg Pro Glu
            435                 440                 445
Pro Glu Pro Arg Pro Pro Thr Thr Thr Pro Gln Pro Thr Ala Pro
    450                 455                 460
Pro Thr Val Cys Pro Thr Gly Pro Pro Thr Val His Pro Ser Glu Arg
465                 470                 475                 480
Pro Thr Ala Gly Pro Thr Gly Pro Pro Ser Ala Gly Pro Thr Gly Pro
                485                 490                 495
Pro Thr Ala Gly Pro Ser Thr Ala Thr Thr Val Pro Leu Ser Pro Val
                500                 505                 510
Asp Asp Ala Cys Asn Val Asn Ile Phe Asp Ala Ile Ala Glu Ile Gly
            515                 520                 525
Asn Gln Leu Tyr Leu Phe Lys Asp Gly Lys Tyr Trp Arg Phe Ser Glu
            530                 535                 540
Gly Arg Gly Ser Arg Pro Gln Gly Pro Phe Leu Ile Ala Asp Lys Trp
545                 550                 555                 560
Pro Ala Leu Pro Arg Lys Leu Asp Ser Val Phe Glu Glu Arg Leu Ser
                565                 570                 575
Lys Lys Leu Phe Phe Phe Ser Gly Arg Gln Val Trp Val Tyr Thr Gly
            580                 585                 590
Ala Ser Val Leu Gly Pro Arg Arg Leu Asp Lys Leu Gly Leu Gly Ala
```

```
            595                 600                 605
Asp Val Ala Gln Val Thr Gly Ala Leu Arg Ser Gly Arg Gly Lys Met
610                 615                 620

Leu Leu Phe Ser Gly Arg Arg Leu Trp Arg Phe Asp Val Lys Ala Gln
625                 630                 635                 640

Met Val Asp Pro Arg Ser Ala Ser Glu Val Asp Arg Met Phe Pro Gly
            645                 650                 655

Val Pro Leu Asp Thr His Asp Val Phe Gln Tyr Arg Glu Lys Ala Tyr
            660                 665                 670

Phe Cys Gln Asp Arg Phe Tyr Trp Arg Val Ser Ser Arg Ser Glu Leu
            675                 680                 685

Asn Gln Val Asp Gln Val Gly Tyr Val Thr Tyr Asp Ile Leu Gln Cys
            690                 695                 700

Pro Glu Asp
705

<210> SEQ ID NO 45
<211> LENGTH: 508
<212> TYPE: PRT
<213> ORGANISM: Homo sapiens

<400> SEQUENCE: 45

Met Asn Cys Gln Gln Leu Trp Leu Gly Phe Leu Leu Pro Met Thr Val
1               5                   10                  15

Ser Gly Arg Val Leu Gly Leu Ala Glu Val Ala Pro Val Asp Tyr Leu
            20                  25                  30

Ser Gln Tyr Gly Tyr Leu Gln Lys Pro Leu Glu Gly Ser Asn Asn Phe
        35                  40                  45

Lys Pro Glu Asp Ile Thr Glu Ala Leu Arg Ala Phe Gln Glu Ala Ser
50                  55                  60

Glu Leu Pro Val Ser Gly Gln Leu Asp Asp Ala Thr Arg Ala Arg Met
65                  70                  75                  80

Arg Gln Pro Arg Cys Gly Leu Glu Asp Pro Phe Asn Gln Lys Thr Leu
                85                  90                  95

Lys Tyr Leu Leu Leu Gly Arg Trp Arg Lys His Leu Thr Phe Arg
            100                 105                 110

Ile Leu Asn Leu Pro Ser Thr Leu Pro Pro His Thr Ala Arg Ala Ala
        115                 120                 125

Leu Arg Gln Ala Phe Gln Asp Trp Ser Asn Val Ala Pro Leu Thr Phe
130                 135                 140

Gln Glu Val Gln Ala Gly Ala Ala Asp Ile Arg Leu Ser Phe His Gly
145                 150                 155                 160

Arg Gln Ser Ser Tyr Cys Ser Asn Thr Phe Asp Gly Pro Gly Arg Val
                165                 170                 175

Leu Ala His Ala Asp Ile Pro Glu Leu Gly Ser Val His Phe Asp Glu
            180                 185                 190

Asp Glu Phe Trp Thr Glu Gly Thr Tyr Arg Gly Val Asn Leu Arg Ile
        195                 200                 205

Ile Ala Ala His Glu Val Gly His Ala Leu Gly Leu Gly His Ser Arg
210                 215                 220

Tyr Ser Gln Ala Leu Met Ala Pro Val Tyr Glu Gly Tyr Arg Pro His
225                 230                 235                 240

Phe Lys Leu His Pro Asp Asp Val Ala Gly Ile Gln Ala Leu Tyr Gly
                245                 250                 255
```

```
Lys Lys Ser Pro Val Ile Arg Asp Glu Glu Glu Thr Glu Leu
            260                 265                 270
Pro Thr Val Pro Pro Val Pro Thr Glu Pro Ser Pro Met Pro Asp Pro
        275                 280                 285
Cys Ser Ser Glu Leu Asp Ala Met Met Leu Gly Pro Arg Gly Lys Thr
290                 295                 300
Tyr Ala Phe Lys Gly Asp Tyr Val Trp Thr Val Ser Asp Ser Gly Pro
305                 310                 315                 320
Gly Pro Leu Phe Arg Val Ser Ala Leu Trp Glu Gly Leu Pro Gly Asn
                325                 330                 335
Leu Asp Ala Ala Val Tyr Ser Pro Arg Thr Gln Trp Ile His Phe Phe
            340                 345                 350
Lys Gly Asp Lys Val Trp Arg Tyr Ile Asn Phe Lys Met Ser Pro Gly
        355                 360                 365
Phe Pro Lys Lys Leu Asn Arg Val Glu Pro Asn Leu Asp Ala Ala Leu
370                 375                 380
Tyr Trp Pro Leu Asn Gln Lys Val Phe Leu Phe Lys Gly Ser Gly Tyr
385                 390                 395                 400
Trp Gln Trp Asp Glu Leu Ala Arg Thr Asp Phe Ser Ser Tyr Pro Lys
                405                 410                 415
Pro Ile Lys Gly Leu Phe Thr Gly Val Pro Asn Gln Pro Ser Ala Ala
            420                 425                 430
Met Ser Trp Gln Asp Gly Arg Val Tyr Phe Phe Lys Gly Lys Val Tyr
        435                 440                 445
Trp Arg Leu Asn Gln Gln Leu Arg Val Glu Lys Gly Tyr Pro Arg Asn
450                 455                 460
Ile Ser His Asn Trp Met His Cys Arg Pro Arg Thr Ile Asp Thr Thr
465                 470                 475                 480
Pro Ser Gly Gly Asn Thr Thr Pro Ser Gly Thr Gly Ile Thr Leu Asp
                485                 490                 495
Thr Thr Leu Ser Ala Thr Glu Thr Phe Glu Tyr
            500                 505

<210> SEQ ID NO 46
<211> LENGTH: 1021
<212> TYPE: PRT
<213> ORGANISM: Clostridium histolyticum

<400> SEQUENCE: 46

Met Lys Arg Lys Cys Leu Ser Lys Arg Leu Met Leu Ala Ile Thr Met
1               5                   10                  15
Ala Thr Ile Phe Thr Val Asn Ser Thr Leu Pro Ile Tyr Ala Ala Val
                20                  25                  30
Asp Lys Asn Asn Ala Thr Ala Ala Val Gln Asn Glu Ser Lys Arg Tyr
            35                  40                  45
Thr Val Ser Tyr Leu Lys Thr Leu Asn Tyr Tyr Asp Leu Val Asp Leu
        50                  55                  60
Leu Val Lys Thr Glu Ile Glu Asn Leu Pro Asp Leu Phe Gln Tyr Ser
65                  70                  75                  80
Ser Asp Ala Lys Glu Phe Tyr Gly Asn Lys Thr Arg Met Ser Phe Ile
                85                  90                  95
Met Asp Glu Ile Gly Arg Arg Ala Pro Gln Tyr Thr Glu Ile Asp His
            100                 105                 110
Lys Gly Ile Pro Thr Leu Val Glu Val Val Arg Ala Gly Phe Tyr Leu
        115                 120                 125
```

-continued

Gly Phe His Asn Lys Glu Leu Asn Glu Ile Asn Lys Arg Ser Phe Lys
    130                 135                 140

Glu Arg Val Ile Pro Ser Ile Leu Ala Ile Gln Lys Asn Pro Asn Phe
145                 150                 155                 160

Lys Leu Gly Thr Glu Val Gln Asp Lys Ile Val Ser Ala Thr Gly Leu
                165                 170                 175

Leu Ala Gly Asn Glu Thr Ala Pro Pro Glu Val Val Asn Asn Phe Thr
            180                 185                 190

Pro Ile Leu Gln Asp Cys Ile Lys Asn Ile Asp Arg Tyr Ala Leu Asp
        195                 200                 205

Asp Leu Lys Ser Lys Ala Leu Phe Asn Val Leu Ala Ala Pro Thr Tyr
210                 215                 220

Asp Ile Thr Glu Tyr Leu Arg Ala Thr Lys Glu Lys Pro Glu Asn Thr
225                 230                 235                 240

Pro Trp Tyr Gly Lys Ile Asp Gly Phe Ile Asn Glu Leu Lys Lys Leu
                245                 250                 255

Ala Leu Tyr Gly Lys Ile Asn Asp Asn Ser Trp Ile Ile Asp Asn
            260                 265                 270

Gly Ile Tyr His Ile Ala Pro Leu Gly Lys Leu His Ser Asn Asn Lys
        275                 280                 285

Ile Gly Ile Glu Thr Leu Thr Glu Val Met Lys Val Tyr Pro Tyr Leu
290                 295                 300

Ser Met Gln His Leu Gln Ser Ala Asp Gln Ile Lys Arg His Tyr Asp
305                 310                 315                 320

Ser Lys Asp Ala Glu Gly Asn Lys Ile Pro Leu Asp Lys Phe Lys Lys
                325                 330                 335

Glu Gly Lys Glu Lys Tyr Cys Pro Lys Thr Tyr Thr Phe Asp Asp Gly
            340                 345                 350

Lys Val Ile Ile Lys Ala Gly Ala Arg Val Glu Glu Lys Val Lys
        355                 360                 365

Arg Leu Tyr Trp Ala Ser Lys Glu Val Asn Ser Gln Phe Phe Arg Val
370                 375                 380

Tyr Gly Ile Asp Lys Pro Leu Glu Glu Gly Asn Pro Asp Asp Ile Leu
385                 390                 395                 400

Thr Met Val Ile Tyr Asn Ser Pro Glu Glu Tyr Lys Leu Asn Ser Val
                405                 410                 415

Leu Tyr Gly Tyr Asp Thr Asn Asn Gly Gly Met Tyr Ile Glu Pro Glu
            420                 425                 430

Gly Thr Phe Phe Thr Tyr Glu Arg Glu Ala Gln Glu Ser Thr Tyr Thr
        435                 440                 445

Leu Glu Glu Leu Phe Arg His Glu Tyr Thr His Tyr Leu Gln Gly Arg
450                 455                 460

Tyr Ala Val Pro Gly Gln Trp Gly Arg Thr Lys Leu Tyr Asp Asn Asp
465                 470                 475                 480

Arg Leu Thr Trp Tyr Glu Glu Gly Gly Ala Glu Leu Phe Ala Gly Ser
                485                 490                 495

Thr Arg Thr Ser Gly Ile Leu Pro Arg Lys Ser Ile Val Ser Asn Ile
            500                 505                 510

His Asn Thr Thr Arg Asn Asn Arg Tyr Lys Leu Ser Asp Thr Val His
        515                 520                 525

Ser Lys Tyr Gly Ala Ser Phe Glu Phe Tyr Asn Tyr Ala Cys Met Phe
530                 535                 540

```
Met Asp Tyr Met Tyr Asn Lys Asp Met Gly Ile Leu Asn Lys Leu Asn
545                 550                 555                 560

Asp Leu Ala Lys Asn Asn Asp Val Asp Gly Tyr Asp Asn Tyr Ile Arg
            565                 570                 575

Asp Leu Ser Ser Asn Tyr Ala Leu Asn Asp Lys Tyr Gln Asp His Met
            580                 585                 590

Gln Glu Arg Ile Asp Asn Tyr Glu Asn Leu Thr Val Pro Phe Val Ala
        595                 600                 605

Asp Asp Tyr Leu Val Arg His Ala Tyr Lys Asn Pro Asn Glu Ile Tyr
        610                 615                 620

Ser Glu Ile Ser Glu Val Ala Lys Leu Lys Asp Ala Lys Ser Glu Val
625                 630                 635                 640

Lys Lys Ser Gln Tyr Phe Ser Thr Phe Thr Leu Arg Gly Ser Tyr Thr
                645                 650                 655

Gly Gly Ala Ser Lys Gly Lys Leu Glu Asp Gln Lys Ala Met Asn Lys
            660                 665                 670

Phe Ile Asp Asp Ser Leu Lys Lys Leu Asp Thr Tyr Ser Trp Ser Gly
        675                 680                 685

Tyr Lys Thr Leu Thr Ala Tyr Phe Thr Asn Tyr Lys Val Asp Ser Ser
    690                 695                 700

Asn Arg Val Thr Tyr Asp Val Phe His Gly Tyr Leu Pro Asn Glu
705                 710                 715                 720

Gly Asp Ser Lys Asn Ser Leu Pro Tyr Lys Ile Asn Gly Thr Tyr
                725                 730                 735

Lys Gly Thr Glu Lys Glu Lys Ile Lys Phe Ser Ser Glu Gly Ser Phe
            740                 745                 750

Asp Pro Asp Gly Lys Ile Val Ser Tyr Glu Trp Asp Phe Gly Asp Gly
        755                 760                 765

Asn Lys Ser Asn Glu Glu Asn Pro Glu His Ser Tyr Asp Lys Val Gly
        770                 775                 780

Thr Tyr Thr Val Lys Leu Lys Val Thr Asp Asp Lys Gly Glu Ser Ser
785                 790                 795                 800

Val Ser Thr Thr Thr Ala Glu Ile Lys Asp Leu Ser Glu Asn Lys Leu
                805                 810                 815

Pro Val Ile Tyr Met His Val Pro Lys Ser Gly Ala Leu Asn Gln Lys
            820                 825                 830

Val Val Phe Tyr Gly Lys Gly Thr Tyr Asp Pro Asp Gly Ser Ile Ala
        835                 840                 845

Gly Tyr Gln Trp Asp Phe Gly Asp Gly Ser Asp Phe Ser Ser Glu Gln
850                 855                 860

Asn Pro Ser His Val Tyr Thr Lys Gly Glu Tyr Thr Val Thr Leu
865                 870                 875                 880

Arg Val Met Asp Ser Ser Gly Gln Met Ser Glu Lys Thr Met Lys Ile
                885                 890                 895

Lys Ile Thr Asp Pro Val Tyr Pro Ile Gly Thr Glu Lys Glu Pro Asn
            900                 905                 910

Asn Ser Lys Glu Thr Ala Ser Gly Pro Ile Val Pro Gly Ile Pro Val
        915                 920                 925

Ser Gly Thr Ile Glu Asn Thr Ser Asp Gln Asp Tyr Phe Tyr Phe Asp
        930                 935                 940

Val Ile Thr Pro Gly Glu Val Lys Ile Asp Ile Asn Lys Leu Gly Tyr
945                 950                 955                 960

Gly Gly Ala Thr Trp Val Val Tyr Asp Glu Asn Asn Asn Ala Val Ser
```

965                 970                 975
Tyr Ala Thr Asp Asp Gly Gln Asn Leu Ser Gly Lys Phe Lys Ala Asp
                    980                 985                 990

Lys Pro Gly Arg Tyr Tyr Ile His Leu Tyr Met Phe Asn Gly Ser Tyr
                995                 1000                1005

Met Pro Tyr Arg Ile Asn Ile Glu Gly Ser Val Gly Arg
    1010                1015                1020

<210> SEQ ID NO 47
<211> LENGTH: 740
<212> TYPE: PRT
<213> ORGANISM: Clostridium histolyticum

<400> SEQUENCE: 47

Met Lys Lys Asn Ile Leu Lys Ile Leu Met Asp Ser Tyr Ser Lys Glu
1               5                   10                  15

Ser Lys Ile Gln Thr Val Arg Val Thr Ser Val Ser Leu Leu Ala
            20                  25                  30

Val Tyr Leu Thr Met Asn Thr Ser Ser Leu Val Leu Ala Lys Pro Ile
            35                  40                  45

Glu Asn Thr Asn Asp Thr Ser Ile Lys Asn Val Glu Lys Leu Arg Asn
        50                  55                  60

Ala Pro Asn Glu Glu Asn Ser Lys Lys Val Glu Asp Ser Lys Asn Asp
65                  70                  75                  80

Lys Val Glu His Val Lys Asn Ile Glu Glu Ala Lys Val Glu Gln Val
                85                  90                  95

Ala Pro Glu Val Lys Ser Lys Ser Thr Leu Arg Ser Ala Ser Ile Ala
            100                 105                 110

Asn Thr Asn Ser Glu Lys Tyr Asp Phe Glu Tyr Leu Asn Gly Leu Ser
        115                 120                 125

Tyr Thr Glu Leu Thr Asn Leu Ile Lys Asn Ile Lys Trp Asn Gln Ile
    130                 135                 140

Asn Gly Leu Phe Asn Tyr Ser Thr Gly Ser Gln Lys Phe Phe Gly Asp
145                 150                 155                 160

Lys Asn Arg Val Gln Ala Ile Ile Asn Ala Leu Gln Glu Ser Gly Arg
                165                 170                 175

Thr Tyr Thr Ala Asn Asp Met Lys Gly Ile Glu Thr Phe Thr Glu Val
            180                 185                 190

Leu Arg Ala Gly Phe Tyr Leu Gly Tyr Tyr Asn Asp Gly Leu Ser Tyr
        195                 200                 205

Leu Asn Asp Arg Asn Phe Gln Asp Lys Cys Ile Pro Ala Met Ile Ala
    210                 215                 220

Ile Gln Lys Asn Pro Asn Phe Lys Leu Gly Thr Ala Val Gln Asp Glu
225                 230                 235                 240

Val Ile Thr Ser Leu Gly Lys Leu Ile Gly Asn Ala Ser Ala Asn Ala
                245                 250                 255

Glu Val Val Asn Asn Cys Val Pro Val Leu Lys Gln Phe Arg Glu Asn
            260                 265                 270

Leu Asn Gln Tyr Ala Pro Asp Tyr Val Lys Gly Thr Ala Val Asn Glu
        275                 280                 285

Leu Ile Lys Gly Ile Glu Phe Asp Phe Ser Gly Ala Ala Tyr Glu Lys
    290                 295                 300

-continued

```
Asp Val Lys Thr Met Pro Trp Tyr Gly Lys Ile Asp Pro Phe Ile Asn
305                 310                 315                 320

Glu Leu Lys Ala Leu Gly Leu Tyr Gly Asn Ile Thr Ser Ala Thr Glu
            325                 330                 335

Trp Ala Ser Asp Val Gly Ile Tyr Tyr Leu Ser Lys Phe Gly Leu Tyr
        340                 345                 350

Ser Thr Asn Arg Asn Asp Ile Val Gln Ser Leu Glu Lys Ala Val Asp
    355                 360                 365

Met Tyr Lys Tyr Gly Lys Ile Ala Phe Val Ala Met Glu Arg Ile Thr
370                 375                 380

Trp Asp Tyr Asp Gly Ile Gly Ser Asn Gly Lys Lys Val Asp His Asp
385                 390                 395                 400

Lys Phe Leu Asp Asp Ala Glu Lys His Tyr Leu Pro Lys Thr Tyr Thr
            405                 410                 415

Phe Asp Asn Gly Thr Phe Ile Ile Arg Ala Gly Asp Lys Val Ser Glu
        420                 425                 430

Glu Lys Ile Lys Arg Leu Tyr Trp Ala Ser Arg Glu Val Lys Ser Gln
    435                 440                 445

Phe His Arg Val Val Gly Asn Asp Lys Ala Leu Glu Val Gly Asn Ala
450                 455                 460

Asp Asp Val Leu Thr Met Lys Ile Phe Asn Ser Pro Glu Glu Tyr Lys
465                 470                 475                 480

Phe Asn Thr Asn Ile Asn Gly Val Ser Thr Asp Asn Gly Gly Leu Tyr
            485                 490                 495

Ile Glu Pro Arg Gly Thr Phe Tyr Thr Tyr Glu Arg Thr Pro Gln Gln
        500                 505                 510

Ser Ile Phe Ser Leu Glu Glu Leu Phe Arg His Glu Tyr Thr His Tyr
    515                 520                 525

Leu Gln Ala Arg Tyr Leu Val Asp Gly Leu Trp Gly Gln Gly Pro Phe
530                 535                 540

Tyr Glu Lys Asn Arg Leu Thr Trp Phe Asp Glu Gly Thr Ala Glu Phe
545                 550                 555                 560

Phe Ala Gly Ser Thr Arg Thr Ser Gly Val Leu Pro Arg Lys Ser Ile
            565                 570                 575

Leu Gly Tyr Leu Ala Lys Asp Lys Val Asp His Arg Tyr Ser Leu Lys
        580                 585                 590

Lys Thr Leu Asn Ser Gly Tyr Asp Asp Ser Asp Trp Met Phe Tyr Asn
    595                 600                 605

Tyr Gly Phe Ala Val Ala His Tyr Leu Tyr Glu Lys Asp Met Pro Thr
610                 615                 620

Phe Ile Lys Met Asn Lys Ala Ile Leu Asn Thr Asp Val Lys Ser Tyr
625                 630                 635                 640

Asp Glu Ile Ile Lys Lys Leu Ser Asp Ala Asn Lys Asn Thr Glu
            645                 650                 655

Tyr Gln Asn His Ile Gln Glu Leu Ala Asp Lys Tyr Gln Gly Ala Gly
        660                 665                 670

Ile Pro Leu Val Ser Asp Asp Tyr Leu Lys Asp His Gly Tyr Lys Lys
    675                 680                 685

Ala Ser Glu Val Tyr Ser Glu Ile Ser Lys Ala Ala Ser Leu Thr Asn
690                 695                 700

Thr Ser Val Thr Ala Glu Lys Ser Gln Tyr Phe Asn Thr Phe Thr Leu
705                 710                 715                 720
```

-continued

```
Arg Gly Thr Tyr Thr Gly Glu Thr Ser Lys Gly Glu Phe Lys Asp Trp
                725                 730                 735

Asp Glu Met Ser
            740
```